US007964191B2

(12) United States Patent
Rodrigues et al.

(10) Patent No.: US 7,964,191 B2

(45) Date of Patent: Jun. 21, 2011

(54) COMPOSITIONS AND METHODS FOR THE TREATMENT OF OPHTHALMIC DISEASE

(75) Inventors: Gerard A. Rodrigues, Laguna Niguel, CA (US); John E. Donello, Dana Point, CA (US); Anne P. McLaughlin, Irvine, CA (US); Fabien J. Schweighoffer, Fontenay-sous-Bois (FR); Florence Mahé, Thiais (FR)

(73) Assignee: Allergan, Inc., Irvine, CA (US)

( * ) Notice: Subject to any disclaimer, the term of this patent is extended or adjusted under 35 U.S.C. 154(b) by 823 days.

(21) Appl. No.: 11/670,883

(22) Filed: Feb. 2, 2007

(65) Prior Publication Data

US 2007/0203089 A1 Aug. 30, 2007

Related U.S. Application Data

(60) Provisional application No. 60/764,892, filed on Feb. 2, 2006.

(51) Int. Cl.

| | |
|---|---|
| ***A61K 39/395*** | (2006.01) |
| ***A61K 39/00*** | (2006.01) |
| ***C07K 16/00*** | (2006.01) |
| ***C07K 16/18*** | (2006.01) |
| ***C07K 16/28*** | (2006.01) |

(52) U.S. Cl. ............... 424/130.1; 424/133.1; 424/135.1; 424/141.1; 424/143.1; 530/387.1; 530/387.3; 530/388.1; 530/388.22

(58) Field of Classification Search ........................ None
See application file for complete search history.

(56) References Cited

U.S. PATENT DOCUMENTS

| | | | | |
|---|---|---|---|---|
| 5,874,082 | A * | 2/1999 | de Boer | 424/153.1 |
| 6,872,714 | B1 | 3/2005 | Schols | |
| 2002/0077339 | A1 | 6/2002 | Bridger et al. | |
| 2004/0018528 | A1 | 1/2004 | Morimoto et al. | |
| 2004/0209837 | A1 | 10/2004 | Kishimoto et al. | |
| 2005/0019927 | A1 | 1/2005 | Hildinger et al. | |
| 2005/0124569 | A1 | 6/2005 | Guerciolini et al. | |
| 2005/0164935 | A1 | 7/2005 | Clark-Lewis et al. | |
| 2005/0265969 | A1 | 12/2005 | Clark-Lewis et al. | |
| 2006/0110429 | A1 | 5/2006 | Reiff et al. | |
| 2006/0257359 | A1 * | 11/2006 | Francois et al. | 424/85.1 |

FOREIGN PATENT DOCUMENTS

| | | |
|---|---|---|
| WO | WO2006/039252 | 4/2006 |
| WO | WO2006/074428 | 7/2006 |
| WO | WO 2006/090853 | 8/2006 |

OTHER PUBLICATIONS

Ochia, Hiroshi, et al., "Preparation of 2-aminopyrimidine compounds as XCR4 antagonists," CA Selects: Anti-Inflammatory Agents & Arthritis, Issue 22, 2006, pp. 77-78.

Butler et al, "SDF-1 is both necessary and sufficient to promote proliferative retinopathy", Journal of Clinical Investigation, vol. 115, No. 1, pp. 86-93, Jan. 8, 2005.

XP009102849, 65-97, Jan. 1, 1900.

* cited by examiner

*Primary Examiner* — Christine J Saoud
*Assistant Examiner* — Jon M Lockard
(74) *Attorney, Agent, or Firm* — Joel B. German; Debra D. Condino; Allergan, Inc.

(57) ABSTRACT

Compositions and methods of treating ocular disorders comprising CXCR4 inhibitory compositions.

13 Claims, 4 Drawing Sheets

SEQUENCE LISTING

<160> NUMBER OF SEQ ID NOS: 55

<210> SEQ ID NO 1
<211> LENGTH: 352
<212> TYPE: PRT
<213> ORGANISM: Homo sapiens

<400> SEQUENCE: 1

Met Glu Gly Ile Ser Ile Tyr Thr Ser Asp Asn Tyr Thr Glu Glu Met
1 5 10 15

Gly Ser Gly Asp Tyr Asp Ser Met Lys Glu Pro Cys Phe Arg Glu Glu
20 25 30

Asn Ala Asn Phe Asn Lys Ile Phe Leu Pro Thr Ile Tyr Ser Ile Ile
35 40 45

Phe Leu Thr Gly Ile Val Gly Asn Gly Leu Val Ile Leu Val Met Gly
50 55 60

Tyr Gln Lys Lys Leu Arg Ser Met Thr Asp Lys Tyr Arg Leu His Leu
65 70 75 80

Ser Val Ala Asp Leu Leu Phe Val Ile Thr Leu Pro Phe Trp Ala Val
85 90 95

Asp Ala Val Ala Asn Trp Tyr Phe Gly Asn Phe Leu Cys Lys Ala Val
100 105 110

His Val Ile Tyr Thr Val Asn Leu Tyr Ser Ser Val Leu Ile Leu Ala
115 120 125

Phe Ile Ser Leu Asp Arg Tyr Leu Ala Ile Val His Ala Thr Asn Ser
130 135 140

Gln Arg Pro Arg Lys Leu Leu Ala Glu Lys Val Val Tyr Val Gly Val
145 150 155 160

Trp Ile Pro Ala Leu Leu Leu Thr Ile Pro Asp Phe Ile Phe Ala Asn
165 170 175

Val Ser Glu Ala Asp Asp Arg Tyr Ile Cys Asp Arg Phe Tyr Pro Asn
180 185 190

Asp Leu Trp Val Val Val Phe Gln Phe Gln His Ile Met Val Gly Leu
195 200 205

Ile Leu Pro Gly Ile Val Ile Leu Ser Cys Tyr Cys Ile Ile Ile Ser
210 215 220

Lys Leu Ser His Ser Lys Gly His Gln Lys Arg Lys Ala Leu Lys Thr
225 230 235 240

Thr Val Ile Leu Ile Leu Ala Phe Phe Ala Cys Trp Leu Pro Tyr Tyr
245 250 255

Ile Gly Ile Ser Ile Asp Ser Phe Ile Leu Leu Glu Ile Ile Lys Gln
260 265 270

Gly Cys Glu Phe Glu Asn Thr Val His Lys Trp Ile Ser Ile Thr Glu
275 280 285

Ala Leu Ala Phe Phe His Cys Cys Leu Asn Pro Ile Leu Tyr Ala Phe
290 295 300

Leu Gly Ala Lys Phe Lys Thr Ser Ala Gln His Ala Leu Thr Ser Val
305 310 315 320

Ser Arg Gly Ser Ser Leu Lys Ile Leu Ser Lys Gly Lys Arg Gly Gly
325 330 335

His Ser Ser Val Ser Thr Glu Ser Glu Ser Ser Ser Phe His Ser Ser
340 345 350

<210> SEQ ID NO 2
<211> LENGTH: 1912
<212> TYPE: DNA
<213> ORGANISM: Homo sapiens

<400> SEQUENCE: 2 tttttttct tccctctagt gggcggggca gaggagttag ccaagatgtg actttgaaac 60
cctcagcgtc tcagtgccct tttgttctaa acaaagaatt ttgtaattgg ttctaccaaa 120
gaaggatata atgaagtcac tatgggaaaa gatggggagg agagttgtag gattctacat 180
taattctctt gtgcccttag cccactactt cagaatttcc tgaagaaagc aagcctgaat 240
tggtttttta aattgcttta aaaatttttt ttaactgggt taatgcttgc tgaattggaa 300
gtgaatgtcc attcctttgc ctcttttgca gatatacact tcagataact acaccgagga 360
aatgggctca ggggactatg actccatgaa ggaaccctgt ttccgtgaag aaaatgctaa 420
tttcaataaa atcttcctgc ccaccatcta ctccatcatc ttcttaactg gcattgtggg 480
caatggattg gtcatcctgg tcatgggtta ccagaagaaa ctgagaagca tgacggacaa 540
gtacaggctg cacctgtcag tggccgacct cctctttgtc atcacgcttc ccttctgggc 600
agttgatgcc gtggcaaact ggtactttgg gaacttccta tgcaaggcag tccatgtcat 660
ctacacagtc aacctctaca gcagtgtcct catcctggcc ttcatcagtc tggaccgcta 720
cctggccatc gtccacgcca ccaacagtca gaggccaagg aagctgttgg ctgaaaaggt 780
ggtctatgtt ggcgtctgga tccctgccct cctgctgact attcccgact tcatctttgc 840
caacgtcagt gaggcagatg acagatatat ctgtgaccgc ttctacccca atgacttgtg 900
ggtggttgtg ttccagtttc agcacatcat ggttggcctt atcctgcctg gtattgtcat 960
cctgtcctgc tattgcatta tcatctccaa gctgtcacac tccaagggcc accagaagcg 1020
caaggccctc aagaccacag tcatcctcat cctggctttc ttcgcctgtt ggctgcctta 1080
ctacattggg atcagcatcg actccttcat cctcctggaa atcatcaagc aagggtgtga 1140
gtttgagaac actgtgcaca agtggatttc catcaccgag gccctagctt tcttccactg 1200
ttgtctgaac ccccatcctct atgctttcct tggagccaaa tttaaaacct ctgcccagca 1260
cgcactcacc tctgtgagca gagggtccag cctcaagatc ctctccaaag gaaagcgagg 1320
tggacattca tctgtttcca ctgagtctga gtcttcaagt tttcactcca gctaacacag 1380
atgtaaaaga cttttttta tacgataaat aacttttttt taagttacac atttttcaga 1440
tataaaagac tgaccaatat tgtacagttt ttattgcttg ttggattttt gtcttgtgtt 1500
tctttagttt ttgtgaagtt taattgactt atttatataa attttttttg tttcatattg 1560
atgtgtgtct aggcaggacc tgtggccaag ttcttagttg ctgtatgtct cgtggtagga 1620
ctgtagaaaa gggaactgaa cattccagag cgtgtagtga atcacgtaaa gctagaaatg 1680
atccccagct gtttatgcat agataatctc tccattcccg tggaacgttt ttcctgttct 1740
taagacgtga ttttgctgta gaagatggca cttataacca aagcccaaag tggtatagaa 1800
atgctggttt ttcagttttc aggagtgggt tgatttcagc acctacagtg tacagtcttg 1860
tattaagttg ttaataaaag tacatgttaa acttaaaaaa aaaaaaaaaa aa 1912

<210> SEQ ID NO 3
<211> LENGTH: 1691
<212> TYPE: DNA

-continued

<213> ORGANISM: Homo sapiens

<400> SEQUENCE: 3

```
aacttcagtt tgttggctgc ggcagcaggt agcaaagtga cgccgagggc ctgagtgctc     60
cagtagccac cgcatctgga gaaccagcgg ttaccatgga ggggatcagt atatacactt    120
cagataacta caccgaggaa atgggctcag gggactatga ctccatgaag gaaccctgtt    180
tccgtgaaga aaatgctaat ttcaataaaa tcttcctgcc caccatctac tccatcatct    240
tcttaactgg cattgtgggc aatggattgg tcatcctggt catgggttac cagaagaaac    300
tgagaagcat gacggacaag tacaggctgc acctgtcagt ggccgacctc ctctttgtca    360
tcacgcttcc cttctgggca gttgatgccg tggcaaactg gtactttggg aacttcctat    420
gcaaggcagt ccatgtcatc tacacagtca acctctacag cagtgtcctc atcctggcct    480
tcatcagtct ggaccgctac ctggccatcg tccacgccac caacagtcag aggccaagga    540
agctgttggc tgaaaaggtg gtctatgttg gcgtctggat ccctgccctc ctgctgacta    600
ttcccgactt catctttgcc aacgtcagtg aggcagatga cagatatatc tgtgaccgct    660
tctaccccaa tgacttgtgg gtggttgtgt tccagtttca gcacatcatg gttggcctta    720
tcctgcctgg tattgtcatc ctgtcctgct attgcattat catctccaag ctgtcacact    780
ccaagggcca ccagaagcgc aaggccctca agaccacagt catcctcatc ctggctttct    840
tcgcctgttg gctgccttac tacattggga tcagcatcga ctccttcatc ctcctggaaa    900
tcatcaagca agggtgtgag tttgagaaca ctgtgcacaa gtggatttcc atcaccgagg    960
ccctagcttt cttccactgt tgtctgaacc ccatcctcta tgctttcctt ggagccaaat   1020
ttaaaacctc tgcccagcac gcactcacct ctgtgagcag agggtccagc ctcaagatcc   1080
tctccaaagg aaagcgaggt ggacattcat ctgtttccac tgagtctgag tcttcaagtt   1140
ttcactccag ctaacacaga tgtaaaagac ttttttttat acgataaata actttttttt   1200
aagttacaca tttttcagat ataaaagact gaccaatatt gtacagtttt tattgcttgt   1260
tggatttttg tcttgtgttt ctttagtttt tgtgaagttt aattgactta tttatataaa   1320
ttttttttgt ttcatattga tgtgtgtcta ggcaggacct gtggccaagt tcttagttgc   1380
tgtatgtctc gtggtaggac tgtagaaaag ggaactgaac attccagagc gtgtagtgaa   1440
tcacgtaaag ctagaaatga tccccagctg tttatgcata gataatctct ccattcccgt   1500
ggaacgtttt tcctgttctt aagacgtgat tttgctgtag aagatggcac ttataaccaa   1560
agcccaaagt ggtatagaaa tgctggtttt tcagttttca ggagtgggtt gatttcagca   1620
cctacagtgt acagtcttgt attaagttgt taataaaagt acatgttaaa cttaaaaaaa   1680
aaaaaaaaaa a                                                        1691
```

<210> SEQ ID NO 4
<211> LENGTH: 89
<212> TYPE: PRT
<213> ORGANISM: Homo sapiens

<400> SEQUENCE: 4

```
Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
```

```
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85


<210> SEQ ID NO 5
<211> LENGTH: 93
<212> TYPE: PRT
<213> ORGANISM: Homo sapiens

<400> SEQUENCE: 5

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90


<210> SEQ ID NO 6
<211> LENGTH: 119
<212> TYPE: PRT
<213> ORGANISM: Homo sapiens

<400> SEQUENCE: 6

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Lys Arg Gln Lys Lys Arg Lys
            100                 105                 110

Ala Ala Gln Lys Arg Lys Asn
        115


<210> SEQ ID NO 7
<211> LENGTH: 1937
<212> TYPE: DNA
<213> ORGANISM: Homo sapiens

<400> SEQUENCE: 7

gcactttcac tctccgtcag ccgcattgcc cgctcggcgt ccggcccccg acccgcgctc      60

gtccgcccgc ccgcccgccc gcccgcgcca tgaacgccaa ggtcgtggtc gtgctggtcc     120

tcgtgctgac cgcgctctgc ctcagcgacg ggaagcccgt cagcctgagc tacagatgcc     180
```

-continued

```
catgccgatt cttcgaaagc catgttgcca gagccaacgt caagcatctc aaaattctca    240

acactccaaa ctgtgccctt cagattgtag cccggctgaa gaacaacaac agacaagtgt    300

gcattgaccc gaagctaaag tggattcagg agtacctgga gaaagcttta aacaagtaag    360

cacaacagcc aaaaaggact ttccgctaga cccactcgag gaaaactaaa accttgtgag    420

agatgaaagg gcaaagacgt gggggagggg gccttaacca tgaggaccag gtgtgtgtgt    480

ggggtgggca cattgatctg ggatcgggcc tgaggtttgc cagcatttag accctgcatt    540

tatagcatac ggtatgatat tgcagcttat attcatccat gccctgtacc tgtgcacgtt    600

ggaactttta ttactggggt ttttctaaga aagaaattgt attatcaaca gcattttcaa    660

gcagttagtt ccttcatgat catcacaatc atcatcattc tcattctcat tttttaaatc    720

aacgagtact tcaagatctg aatttggctt gtttggagca tctcctctgc tcccctgggg    780

agtctgggca cagtcaggtg gtggcttaac agggagctgg aaaaagtgtc ctttcttcag    840

acactgaggc tcccgcagca gcgcccctcc caagaggaag gcctctgtgg cactcagata    900

ccgactgggg ctgggcgccg ccactgcctt cacctcctct ttcaacctca gtgattggct    960

ctgtgggctc catgtagaag ccactattac tgggactgtg ctcagagacc cctctcccag   1020

ctattcctac tctctccccg actccgagag catgcttaat cttgcttctg cttctcattt   1080

ctgtagcctg atcagcgccg caccagccgg gaagagggtg attgctgggg ctcgtgccct   1140

gcatccctct cctcccaggg cctgccccac agctcgggcc ctctgtgaga tccgtctttg   1200

gcctcctcca gaatggagct ggccctctcc tggggatgtg taatggtccc cctgcttacc   1260

cgcaaaagac aagtctttac agaatcaaat gcaattttaa atctgagagc tcgctttgag   1320

tgactgggtt ttgtgattgc ctctgaagcc tatgtatgcc atggaggcac taacaaactc   1380

tgaggtttcc gaaatcagaa gcgaaaaaat cagtgaataa accatcatct tgccactacc   1440

ccctcctgaa gccacagcag ggtttcaggt tccaatcaga actgttggca aggtgacatt   1500

tccatgcata aatgcgatcc acagaaggtc ctggtggtat ttgtaacttt ttgcaaggca   1560

tttttttata tatattttg tgcacatttt tttttacgtt tctttagaaa acaaatgtat   1620

ttcaaaatat atttatagtc gaacaattca tatatttgaa gtggagccat atgaatgtca   1680

gtagtttata cttctctatt atctcaaact actggcaatt tgtaaagaaa tatatatgat   1740

atataaatgt gattgcagct tttcaatgtt agccacagtg tatttttca cttgtactaa   1800

aattgtatca aatgtgacat tatatgcact agcaataaaa tgctaattgt ttcatggtat   1860

aaacgtccta ctgtatgtgg gaatttattt acctgaaata aaattcatta gttgttagtg   1920

atggagctta aaaaaaa                                                  1937
```

<210> SEQ ID NO 8
<211> LENGTH: 3542
<212> TYPE: DNA
<213> ORGANISM: Homo sapiens

<400> SEQUENCE: 8

```
gcactttcac tctccgtcag ccgcattgcc cgctcggcgt ccggccccg acccgcgctc     60

gtccgcccgc ccgcccgccc gcccgcgcca tgaacgccaa ggtcgtggtc gtgctggtcc    120

tcgtgctgac cgcgctctgc ctcagcgacg ggaagcccgt cagcctgagc tacagatgcc    180

catgccgatt cttcgaaagc catgttgcca gagccaacgt caagcatctc aaaattctca    240

acactccaaa ctgtgccctt cagattgtag cccggctgaa gaacaacaac agacaagtgt    300

gcattgaccc gaagctaaag tggattcagg agtacctgga gaaagcttta aacaagaggt    360
```

-continued

```
tcaagatgtg agagggtcag acgcctgagg aacccttaca gtaggagccc agctctgaaa    420
ccagtgttag ggaagggcct gccacagcct cccctgccag ggcagggccc caggcattgc    480
caagggcttt gttttgcaca ctttgccata ttttcaccat ttgattatgt agcaaaatac    540
atgacattta tttttcattt agtttgatta ttcagtgtca ctggcgacac gtagcagctt    600
agactaaggc cattattgta cttgccttat tagagtgtct ttccacggag ccactcctct    660
gactcagggc tcctgggttt tgtattctct gagctgtgca ggtggggaga ctgggctgag    720
ggagcctggc cccatggtca gccctagggt ggagagccac caagagggac gcctgggggt    780
gccaggacca gtcaacctgg gcaaagccta gtgaaggctt ctctctgtgg gatgggatgg    840
tggagggcca catgggaggc tcaccccctt ctccatccac atgggagccg ggtctgcctc    900
ttctgggagg gcagcagggc taccctgagc tgaggcagca gtgtgaggcc agggcagagt    960
gagacccagc cctcatcccg agcacctcca catcctccac gttctgctca tcattctctg   1020
tctcatccat catcatgtgt gtccacgact gtctccatgg ccccgcaaaa ggactctcag   1080
gaccaaagct ttcatgtaaa ctgtgcacca agcaggaaat gaaaatgtct tgtgttacct   1140
gaaaacactg tgcacatctg tgtcttgttt ggaatattgt ccattgtcca atcctatgtt   1200
tttgttcaaa gccagcgtcc tcctctgtga ccaatgtctt gatgcatgca ctgttccccc   1260
tgtgcagccg ctgagcgagg agatgctcct tgggcccttt gagtgcagtc ctgatcagag   1320
ccgtggtcct ttggggtgaa ctaccttggt tcccccactg atcacaaaaa catggtgggt   1380
ccatgggcag agcccaaggg aattcggtgt gcaccagggt tgaccccaga ggattgctgc   1440
cccatcagtg ctccctcaca tgtcagtacc ttcaaactag ggccaagccc agcactgctt   1500
gaggaaaaca agcattcaca acttgttttt ggtttttaaa acccagtcca caaaataacc   1560
aatcctggac atgaagattc tttcccaatt cacatctaac ctcatcttct tcaccatttg   1620
gcaatgccat catctcctgc cttcctcctg ggccctctct gctctgcgtg tcacctgtgc   1680
ttcgggccct tcccacagga catttctcta agagaacaat gtgctatgtg aagagtaagt   1740
caacctgcct gacatttgga gtgttcccct tccactgagg gcagtcgata gagctgtatt   1800
aagccactta aaatgttcac ttttgacaaa ggcaagcact tgtgggtttt tgttttgttt   1860
ttcattcagt cttacgaata cttttgccct ttgattaaag actccagtta aaaaaaattt   1920
taatgaagaa agtggaaaac aaggaagtca aagcaaggaa actatgtaac atgtaggaag   1980
taggaagtaa attatagtga tgtaatcttg aattgtaact gttcttgaat ttaataatct   2040
gtagggtaat tagtaacatg tgttaagtat tttcataagt atttcaaatt ggagcttcat   2100
ggcagaaggc aaacccatca acaaaaattg tcccttaaac aaaaattaaa atcctcaatc   2160
cagctatgtt atattgaaaa aatagagcct gagggatctt tactagttat aaagatacag   2220
aactctttca aaacctttttg aaattaacct ctcactatac cagtataatt gagttttcag   2280
tggggcagtc attatccagg taatccaaga tattttaaaa tctgtcacgt agaacttgga   2340
tgtacctgcc cccaatccat gaaccaagac cattgaattc ttggttgagg aaacaaacat   2400
gaccctaaat cttgactaca gtcaggaaag gaatcatttc tatttctcct ccatgggaga   2460
aaatagataa gagtagaaac tgcagggaaa attatttgca taacaattcc tctactaaca   2520
atcagctcct tcctggagac tgcccagcta aagcaatatg catttaaata cagtcttcca   2580
tttgcaaggg aaaagtctct tgtaatccga atctcttttt gctttcgaac tgctagtcaa   2640
gtgcgtccac gagctgttta ctagggatcc ctcatctgtc cctccgggac ctggtgctgc   2700
ctctacctga cactcccttg ggctccctgt aacctcttca gaggccctcg ctgccagctc   2760
```

-continued

```
tgtatcagga cccagaggaa ggggccagag gctcgttgac tggctgtgtg ttgggattga   2820

gtctgtgcca cgtgtttgtg ctgtggtgtg tccccctctg tccaggcact gagataccag   2880

cgaggaggct ccagagggca ctctgcttgt tattagagat tacctcctga gaaaaaaggt   2940

tccgcttgga gcagaggggc tgaatagcag aaggttgcac ctcccccaac cttagatgtt   3000

ctaagtcttt ccattggatc tcattggacc cttccatggt gtgatcgtct gactggtgtt   3060

atcaccgtgg gctccctgac tgggagttga tcgcctttcc caggtgctac accctttcc   3120

agctggatga gaatttgagt gctctgatcc ctctacagag cttccctgac tcattctgaa   3180

ggagccccat tcctgggaaa tattccctag aaacttccaa atcccctaag cagaccactg   3240

ataaaaccat gtagaaaatt tgttattttg caacctcgct ggactctcag tctctgagca   3300

gtgaatgatt cagtgttaaa tgtgatgaat actgtatttt gtattgtttc aattgcatct   3360

cccagataat gtgaaaatgg tccaggagaa ggccaattcc tatacgcagc gtgctttaaa   3420

aaataaataa gaaacaactc tttgagaaac aacaatttct actttgaagt cataccaatg   3480

aaaaaatgta tatgcactta taattttcct aataaagttc tgtactcaaa tgtagccacc   3540

aa                                                                 3542
```

```
<210> SEQ ID NO 9
<211> LENGTH: 471
<212> TYPE: DNA
<213> ORGANISM: Homo sapiens

<400> SEQUENCE: 9

gcactttcac tctccgtcag ccgcattgcc cgctcggcgt ccggcccccg acccgcgctc     60

gtccgcccgc ccgcccgccc gcccgcgcca tgaacgccaa ggtcgtggtc gtgctggtcc    120

tcgtgctgac cgcgctctgc ctcagcgacg ggaagcccgt cagcctgagc tacagatgcc    180

catgccgatt cttcgaaagc catgttgcca gagccaacgt caagcatctc aaaattctca    240

acactccaaa ctgtgccctt cagattgtag cccggctgaa gaacaacaac agacaagtgt    300

gcattgaccc gaagctaaag tggattcagg agtacctgga gaaagcttta aacaaggggc    360

gcagagaaga aaaagtgggg aaaaaagaaa agataggaaa aaagaagcga cagaagaaga    420

gaaaggctgc ccagaaaagg aaaaactagt tatctgccac ctcgagatgg a             471
```

```
<210> SEQ ID NO 10
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 10

aacaguggaa gaaagcuagg ggcuc                                           25
```

```
<210> SEQ ID NO 11
<211> LENGTH: 25
<212> TYPE: RNA
<213> ORGANISM: Artificial sequence
<220> FEATURE:
<223> OTHER INFORMATION: anti CXCR4 siRNA

<400> SEQUENCE: 11

gaggcccuag cuuucuucca cuguu                                           25
```

```
<210> SEQ ID NO 12
<211> LENGTH: 25
<212> TYPE: RNA
```

<213> ORGANISM: Artificial sequence
<220> FEATURE:
<223> OTHER INFORMATION: anti CXCR4 siRNA

<400> SEQUENCE: 12
aacaguggaa gaaagcuagg gccuc 25

<210> SEQ ID NO 13
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 13
gaggcccuag cuuucuucca cuguu 25

<210> SEQ ID NO 14
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 14
cuuggagugu gacagcuugg agaug 25

<210> SEQ ID NO 15
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 15
caucuccaag cugucacacu ccaag 25

<210> SEQ ID NO 16
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 16
ccagagccaa cgucaagcau cucaa 25

<210> SEQ ID NO 17
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 17
uugagaugcu ugacguuggc ucugg 25

<210> SEQ ID NO 18
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 18
cagagccaac gucaagcauc ucaaa 25

-continued

<210> SEQ ID NO 19
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 19
uuugagaugc uugacguugg cucug 25

<210> SEQ ID NO 20
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 20
acacuccaaa cugugcccuu cagau 25

<210> SEQ ID NO 21
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 21
aucugaaggg cacaguuugg agugu 25

<210> SEQ ID NO 22
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 22
caagugugca uugacccgaa gcuaa 25

<210> SEQ ID NO 23
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 23
uuagcuucgg gucaaugcac acuug 25

<210> SEQ ID NO 24
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 24
aagugugcau ugacccgaag cuaaa 25

<210> SEQ ID NO 25
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 25
uuuagcuucg ggucaaugca cacuu 25

<210> SEQ ID NO 26
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 26
cauugacccg aagcuaaagu ggauu 25

<210> SEQ ID NO 27
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 27
aauccacuuu agcuucgggu caaug 25

<210> SEQ ID NO 28
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 28
cgaagcuaaa guggauucag gagua 25

<210> SEQ ID NO 29
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 29
uacuccugaa uccacuuuag cuucg 25

<210> SEQ ID NO 30
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 30
ucaggaguac cuggagaaag cuuua 25

<210> SEQ ID NO 31
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 31
uaaagcuuuc uccagguacu ccuga 25

<210> SEQ ID NO 32
<211> LENGTH: 25
<212> TYPE: RNA

-continued

<213> ORGANISM: Artificial sequence
<220> FEATURE:
<223> OTHER INFORMATION: anti-SDF-1 siRNA

<400> SEQUENCE: 32
caggaguacc uggagaaagc uuuaa 25

<210> SEQ ID NO 33
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 33
uuaaagcuuu cuccagguac uccug 25

<210> SEQ ID NO 34
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 34
aggaguaccu ggagaaagcu uuaaa 25

<210> SEQ ID NO 35
<211> LENGTH: 25
<212> TYPE: RNA
<213> ORGANISM: Artificial sequence
<220> FEATURE:
<223> OTHER INFORMATION: anti-SDF-1 siRNA

<400> SEQUENCE: 35
uuuaaagcuu ucuccaggua cuccu 25

<210> SEQ ID NO 36
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 36
cccaccaucu acuccaucau cuucu 25

<210> SEQ ID NO 37
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 37
agaagaugau ggaguagaug guggg 25

<210> SEQ ID NO 38
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 38
accaucuacu ccaucaucuu cuuaa 25

-continued

<210> SEQ ID NO 39
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 39
uuaagaagau gauggaguag auggu 25

<210> SEQ ID NO 40
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 40
caucaucuuc uuaacuggca uugug 25

<210> SEQ ID NO 41
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 41
cacaaugcca guuaagaaga ugaug 25

<210> SEQ ID NO 42
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 42
ggcaauggau uggucauccu gguca 25

<210> SEQ ID NO 43
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 43
ugaccaggau gaccaaucca uugcc 25

<210> SEQ ID NO 44
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 44
ugguuggccu uauccugccu gguau 25

<210> SEQ ID NO 45
<211> LENGTH: 25
<212> TYPE: RNA
<213> ORGANISM: Artificial sequence
<220> FEATURE:
<223> OTHER INFORMATION: anti-CXCR4 siRNA -continued

<400> SEQUENCE: 45
auaccaggca ggauaaggcc aacca 25

<210> SEQ ID NO 46
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 46
ucuucgccug uuggcugccu uacua 25

<210> SEQ ID NO 47
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 47
uaguaaggca gccaacaggc gaaga 25

<210> SEQ ID NO 48
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 48
cgccuguugg cugccuuacu acauu 25

<210> SEQ ID NO 49
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 49
aauguaguaa ggcagccaac aggcg 25

<210> SEQ ID NO 50
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 50
gaggcccuag cuuucuucca cuguu 25

<210> SEQ ID NO 51
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 51
aacaguggaa gaaagcuagg gccuc 25

<210> SEQ ID NO 52
<211> LENGTH: 25
<212> TYPE: RNA

-continued

```
<213> ORGANISM: Artificial sequence
<220> FEATURE:
<223> OTHER INFORMATION: anti-CXCR4 siRNA

<400> SEQUENCE: 52

caaaggaaag cgagguggac auuca                                   25


<210> SEQ ID NO 53
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 53

ugaaugucca ccucgcuuuc cuuug                                   25


<210> SEQ ID NO 54
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 54

aaagcgaggu ggacauucau cuguu                                   25


<210> SEQ ID NO 55
<211> LENGTH: 25
<212> TYPE: RNA
<213> ORGANISM: Artificial sequence
<220> FEATURE:
<223> OTHER INFORMATION: anti-CXCR4 siRNA

<400> SEQUENCE: 55

aacagaugaa uguccaccuc gcuuu                                   25
```

COMPOSITIONS AND METHODS FOR THE TREATMENT OF OPHTHALMIC DISEASE

This application claims the benefit of priority from U.S. Patent Application No. 60/764,892, filed on Feb. 2, 2006, the contents of which are incorporated by reference.

BACKGROUND OF THE INVENTION

Approximately one of every 247 (over 1.1 million people) people is legally blind in the United States, Worldwide it is estimated that 42,000,000 people are affected by blindness—either total or nearly so. Additional large numbers of people suffer from other severe retinal disorders.

Blindness in the developing world is often preventable. For example, a study of blindness in India reveals that 62% is caused by cataracts, 19% by refractive error, 5.8% by untreated glaucoma.

However, retinal disorders, including without limitation, diabetic retinopathy, retinitis pigmentosa (RP), wet and dry age-related macular degeneration (ARMD), inflammatory disease including macular edema, central vein occlusion, uveitis affecting the retina, and proliferative vitreoretinopathy are much more prevalent causes of blindness in the Western world.

Diabetic retinopathy is another common form of retinal disease. While diet, exercise, and drug therapy can do much to lessen the ocular effects of diabetes on the retina, there is no specific cure or prophylactic for diabetic retinopathy.

Similarly, glaucoma is a condition that is most commonly (though not exclusively) characterized by high intraocular pressure and which also involves degeneration of the retinal and optic nerve. While high intraocular pressure is susceptible to management with, for example, β adrenergic receptor antagonists such as timolol and α adrenergic receptor agonists such as brimonidine, the neural degeneration that accompanies glaucoma is neither reversible nor can it be definitively halted by lowering intraocular pressure alone.

In the developed world, by far the major retinal disease causing blindness in adults over 60 is age related macular degeneration (AMD), and with the segment of the population within this age range steadily increasing in the United States, the number of cases are likely to increase by the same rate without an effective treatment for the condition.

AMD progressively decreases the function of specific neural and epithelial layers of the retinal macula. The clinical presentation of the condition includes the presence of drusen, hyperplasia of the retinal pigmented epithelium (RPE), geographic atrophy, and choroidal neovascularization (CNV). Atrophic AMD is characterized by outer retinal and RPE atrophy and subadjacent choriocapillaris degeneration, and accounts for about 25% of cases with severe central visual loss.

Exudative (or "wet") AMD is characterized by CNV growth under the RPE and retina, and subsequent hemorrhage, exudive retinal detachment, diciform scarring, and retinal atrophy. Pigment epithelial detachment can also occur. Exudative AMD accounts for about 75% of AMD cases with severe central vision loss.

Currently most treatment for this disease involves therapies that are most helpful to patients who are suffering from relatively advanced symptoms of the disease. These therapies include laser photocoagulation, photodynamic therapy and surgery in cases where CNV is involved. However, there is no currently effective therapy for the early stages of the disease.

It is known that inflammation, particularly chronicchromic inflammation, plays a large part in the development of AMD.

Drusen, the presence of which is one of the hallmarks of AMD, comprise protein and cellular components including immunoglobulin and components of the complement pathways that are involved in immune complex deposition, molecules involved in acute response to inflammation such as α1-antitrypsin and amyloid P component; major histocompatibility complex class II antigens. Additionally, drusen include RPE fragments, melanin and lipofuscin. Some researchers have suggested that the presence of vitronectin, apolipoprotein E and other drusen-associated molecules indicates that the RPE cells are subject to a chronic, sub-lethal complement attack. Such an attack may result in the elimination of surface-associated membrane attack complexes (such as by shedding or endocytosis of cell membrane) and the formation of extracellular deposits of immune complexes and complement components, activated macrophages and other inflammatory cells secrete enzymes that can damage cells and degrade the Bruch membrane (the inner layer of the choroid in contact with the RPE). By releasing cytokines, inflammatory cells may encourage CNV growth in the sub-RPE space.

Interestingly, complement activation and associated inflammatory events occur in other diseases that exhibit cellular degeneration and accumulation of abnormal tissue deposits, such as arthrosclerosis and Alzheimer disease. Indeed, the Alzheimer β-amyloid peptide is found together with activated complement components in a sub structural vesicular component with drusen.

Intravitreal administration of corticosteroid appears to reduce the incidence of CNS infiltration in primates. This may be due to the known anti-inflammatory activity of steroids, which may alter inflammatory cell activity in the choroid. However, chronic use of steroids can have serious side effects, including glucose intolerance, diabetes and weight gain.

Initiation of an inflammatory response involves the detection of an injury, other insult, or infection by members of the host immune surveillance system, comprising immune cells that are involved in trafficking around the body. Immune cell trafficking involves circulation, homing and adhesion, extravasation (entry of the leukocyte through the endothelial barrier), and movement of particular populations of leukocytes between the blood vessels, lymph and lymphatic organs and the tissues.

Trafficking is regulated by a complex interaction of cellular adhesion molecules ((such as integrins and selectins) and of a family of cytokines, termed chemokines, and their receptors.

Chemokines comprise a large family of chemoattractant molecules that function in part to guide phagocytotic leukocytes of the immune system to injured or infected tissue. Two groups of chemoattractants have been identified to date; the first group comprises "classical" chemoattractants including bacterially-derived N-formyl peptides, complement fragment peptides C5a and C3a, and lipids such as leukotriene B4 and platelet-activating factor.

The second, more recently characterized group of chemoattractants comprises a superfamily of chemotactic cytokines having molecular weights of from about 8 to about 17 KDa. These chemokines are secreted proteins that function in leukocyte trafficking, recruiting, and recirculation. They have also been discovered to play a critical role in many pathophysiological processes such as allergic responses, infectious and autoimmune diseases, angiogenesis, inflammation, tumor growth, and hematopoietic development. Approximately 80 percent of these proteins have from 66 to 78 amino acids in their mature form comprising a core region of relative homogeneity. The remaining chemokines are of larger molecular weight, with additional amino acids occurring upstream of the protein "core", or as part of an extended C-terminal segment.

All chemokines signal through the chemokine subfamily of seven transmembrane domain G-protein coupled receptors (GPCRs). GPCRs constitute the single largest family of signal detectors at the cell surface. Activation of GPCRs by selective or specific ligands triggers signal propagation via the G proteins, which subsequently regulate the activities of downstream effector molecules within the target cell. G proteins are so named because they can bind to and are activated by guanidine triphosphate (GTP).

The fidelity of GPCR-mediated signal transduction is maintained at several levels. Firstly, the ligand-receptor interaction is highly selective where discrimination of ligand stereoisomers is commonly observed. Secondly, each GPCR can generally only interact with a small subset of G proteins, which in turn regulate a limited number of effectors. The G proteins are classified into four subfamilies termed Gs, Gi, Gq and G12, according to their sequence homologies.

The intact G holoproteins are heterotrimeric polypeptides. The guanidine diphosphate (GDP)-bound form of the heterotrimeric G protein is inactive, while the GTP-bound form is active. Upon ligand binding to the GPCR, the receptor undergoes a change in conformation that results in the recruitment of the inactive heterotrimeric G protein to the ligand-bound GPCR. Once bound to the receptor, the α subunit of the G protein expels the bound GDP, replaces the GDP with GTP and, so activated, the α subunit of the G protein now dissociates from the tightly associated Gβ and Gγ subunit (or "βγ") dimer. The βγ dimer is then free to interact with and regulate various effectors. Similarly, the activated α subunit can then, for example, bind to and stimulate adenylyl cyclase, that in turn regulates the catalytic production of cAMP. Alternatively, if the G protein is a Gq trimer, the activated α subunit can bind to and regulate PLC.

The primary structures of all the Gq family α subunits share high percentages of identity with each other and they also share common functional properties. They can regulate the activity of phospholipase C isoforms (PLC) through selective activation by GPCRs. This leads to an increase in the intracellular level of inositol phosphates (IP).

The GPCRs are members of the class of receptors known as "serpentine" receptors. Helical domains of these structurally related receptors cross the plasma membrane seven times and possess an extracellular amino terminus and intracellular carboxyl terminus. G protein-coupled receptors are estimated to occur in more than 1000 variations in mammals and regulate some activity in nearly every human cell. Members of the G protein-coupled receptor superfamily include, without limitation, the alpha adrenergic, beta-adrenergic, dopamine, muscarinic, acetylcholine, nicotinic acetylcholine, rhodopsin, opioid, somatostatin, and serotonin receptors.

There are currently at least seventeen known chemokine receptors, and many of these receptors exhibit promiscuous binding properties, whereby several different chemokines can signal through the same receptor. The chemokine receptors are approximately 350 amino acids in length and can be aligned with each other only if gaps are introduced into the primary "universal" sequence. The N terminus is acidic and extracellular can be sulfated and contain N-linked glycosylation sites. The C terminus is intracellular and comprises serine and threonine residues capable of being phosphorylated for receptor regulation. The seven transmembrane domains are linked by three intracellular and three extracellular loops of hydrophilic residues. The highly conserved cysteines in the $1^{st}$ and $2^{nd}$ extracellular loops are joined in a disulfide bond. The G proteins couple to the receptors by way of the C-terminus and perhaps the third intracellular loop.

The chemokine receptor ligands are divided into subfamilies based on conserved amino acid sequence motifs. Most chemokine family members have at least four conserved cysteine residues that form two intramolecular disulfide bonds. The subfamilies are defined by the position of the first two cysteine residues, Thus:

a) The alpha (α) subfamily, also called the CXC chemokines, have one amino acid ("X", designating that any amino acid may occupy this position) separating the first two cysteine residues. This group can be further subdivided based on the presence or absence of a Glu-Leu-Arg (ELR) amino acid motif immediately preceding the first cysteine residue. There are currently five CXC-specific receptors and they are designated CXCR1 to CXCR5. The ELR chemokines bind to CXCR1 and/or CXCR2 and generally act as neutrophil chemoattractants and activators. At present, 14 different human genes encoding CXC chemokines have been reported in the scientific literature with some additional diversity contributed by alternative splicing.

b) In the beta (β) subfamily, also called the CC chemokines, the first two cysteines are adjacent to one another with no intervening amino acid. There are currently 24 distinct human β subfamily members. The receptors for this group are designated CCR1 to CCR11. Target cells for different CC family members include most types of leukocytes.

c) There are two known proteins with chemokine homology that fall outside of the α and β subfamilies. Lymphotactin is the lone member of the gamma (γ) class (C chemokine) which has lost the first and third cysteines. The lymphotactin receptor is designated XCR1. Fractalkine, the only currently known member of the delta (δ) class (CXC chemokine), has three intervening amino acids between the first two cysteine residues. This molecule is unique among chemokines in that it is a transmembrane protein with the N-terminal chemokine domain fused to a long mucin-like stalk. The fractalkine receptor is known as CXCR1.

A variety of approaches have been used to identify chemokines. The earliest discoveries of chemokines were made as a result of their biological activity or through studies that sought to identify proteins that are upregulated following cell activation or differentially expressed in selected cell types. Most of the recently reported chemokines, however, were identified through bioinformatics. EST (Expressed Sequence Tags) databases contain the sequences of a large number of cDNA fragments from a variety of tissues and organisms. Translation of ESTs can provide partial amino acid sequences of the proteome. Because the chemokines are comparatively small and contain signature amino acid motifs, many novel family members have been identified through searches of EST databases.

The stromal cell-derived factors SDF-1α and SDF-1β are CXC chemokines encoded by alternatively spliced mRNAs. The mature α and β forms differ only in that the β form has four additional amino acids at its C-terminus. These proteins are highly conserved between species. Most functional studies have been performed with SDF-1α and suggest a variety of roles for this molecule. It is necessary for normal development of B cells and brain. It is a potent chemoattractant for CD34 bone marrow progenitor cells and dendritic cells. It also appears to play a role in trafficking and adhesion of lymphocytes and megakaryocytes.

An additional alternatively-spliced product from rat, designated SDF-1γ, was reported recently. The SDF-1γ mRNA is similar to the SDF-1β message but with an additional exon inserted near the C-terminal end of the coding region. The four amino acids of SDF-1β that are normally appended to the C-terminus of SDF-1α are replaced in SDF-1γ by a 30 amino acid segment containing 17 positively charged residues. The SDF-1β and 1γβ transcripts display different patterns of expression in a number of tissues. They are also reciprocally expressed in developing rat brain. SDF-1β is expressed in embryonic and neonatal brain, whereas SDF-1γ is expressed in adult brain. The function of this variant is still currently unknown.

A unique chemotactic activity was recently reported for SDF-1 in which subpopulations of T cells were attracted by SDF-1α concentrations of 100 ng/mL but repelled by concentrations of 1 μg/mL. The higher concentration that elicited repulsion is comparable to the concentration of SDF-1 that occurs in the bone marrow. Inhibitor studies reveal that migration in both directions requires the CXCR4 receptor, G-proteins, and phosphatidylinositol 3-kinase. However, tyrosine kinase inhibitors block chemoattraction and have no affect on chemorepulsion, whereas a cAMP agonist inhibits chemorepulsion but does not affect chemoattraction.

CD34 is a cell-surface marker that correlates in humans with bone marrow progenitors having a high proliferative response to hematopoietic cytokines. $CD34^+$ hematopoietic progenitor cells (HPC) have been observed to migrate both in vitro and in vivo toward a gradient of SDF-1 produced by structural bone marrow cells called stromal cells. In the in vivo experiments, the SDF-1 was administered to the spleen. See Aiuti et al., 185 *J. Exp. Med.* 111 (Jan. 6, 1997); this and all other references cited in this patent application are hereby incorporated by reference herein in their entirety.

Myeloid and erythroid cells, as well as B- and T-lymphoid cells, have been found in cultures of cells having the $CD34^+$ phenotype. The concentrations of SDF-1 that stimulate a chemotactic response also cause a transient elevation of $Ca^{++}$ in $CD34^+$ cells. $CD34^+$ cells have been demonstrated to be able to reconstitute blood cells in lethally irradiated baboons and in humans. Pertussis toxin completely inhibited the SDF-1 induced chemotaxis, indicating that the chemokine receptor present in $CD34^+$ cells processes SDF-1 signals through Gi. SDF-1 attracts CFU-GM (granulocyte/macrophage colony forming units), CFU-MIX (colony forming units of mixed lineage and BFU-E (erythroid burst-forming units) progenitor cells from human bone marrow (BM), umbilical cord blood (CB) and mobilized peripheral blood (PB). There is a high degree of conservation between human and mouse SDF-1 (a single amino acid difference), and mouse SDF-1 causes transendothelial chemotaxis on both human and mouse HPC.

Interestingly, HPCs have been identified as being capable of differentiating into liver cells. When clinical liver or bone marrow transplantation occurs, occasionally BM-derived hepatocytes have been found. While the number of HPCs that engraft irradiated liver and develop into hepatocyte-like, albumin-producing cells is extremely low, when the liver is injured or challenged by viral inflammation, the number of such cells increases in response to the stress. In mice there is a very large amplification of HPCs that have at least some of the hallmarks of hepatic morphology and function.

SDF-1, which is also known as CXCL12, is widely expressed in various tissues during both development an adulthood, and these tissues include the liver. Stress, caused by injury, infection or insult, can facilitate tissue-specific differentiation and induce secretion of signaling mediators that increase migration and guide transplanted pluripotent stem cells to the injured tissue. Also, there is increased expression of SDF-1 in the liver after the entire body is irradiated. In humans, those patients injected with HCV, expression of SDF-1 is extended to bile ductile tissue, canal of Hering, and oval cells.

This stress-related increase in SDF-1 expression appears to be associated with some factors including matrix metalloproteases MMP-9 and MMP-2. These proteases are activated following $CCl_4$-mediated liver injury, and this phenomenon in turn triggers mobilization of human progenitor cells from the marrow into general circulation. At the same time the levels of CXCR4 receptor expression increase.

Guerciolini et al., U.S. Patent Application Publication 2006/0019917 discloses siRNA interference of a stromal cell derived factor-1 isoform.

All publications cited in this application are hereby incorporated by reference herein in their entirety, regardless whether an express incorporation by reference is made along with a citation of the reference or not.

DETAILED DESCRIPTION OF THE INVENTION

Figure 1:
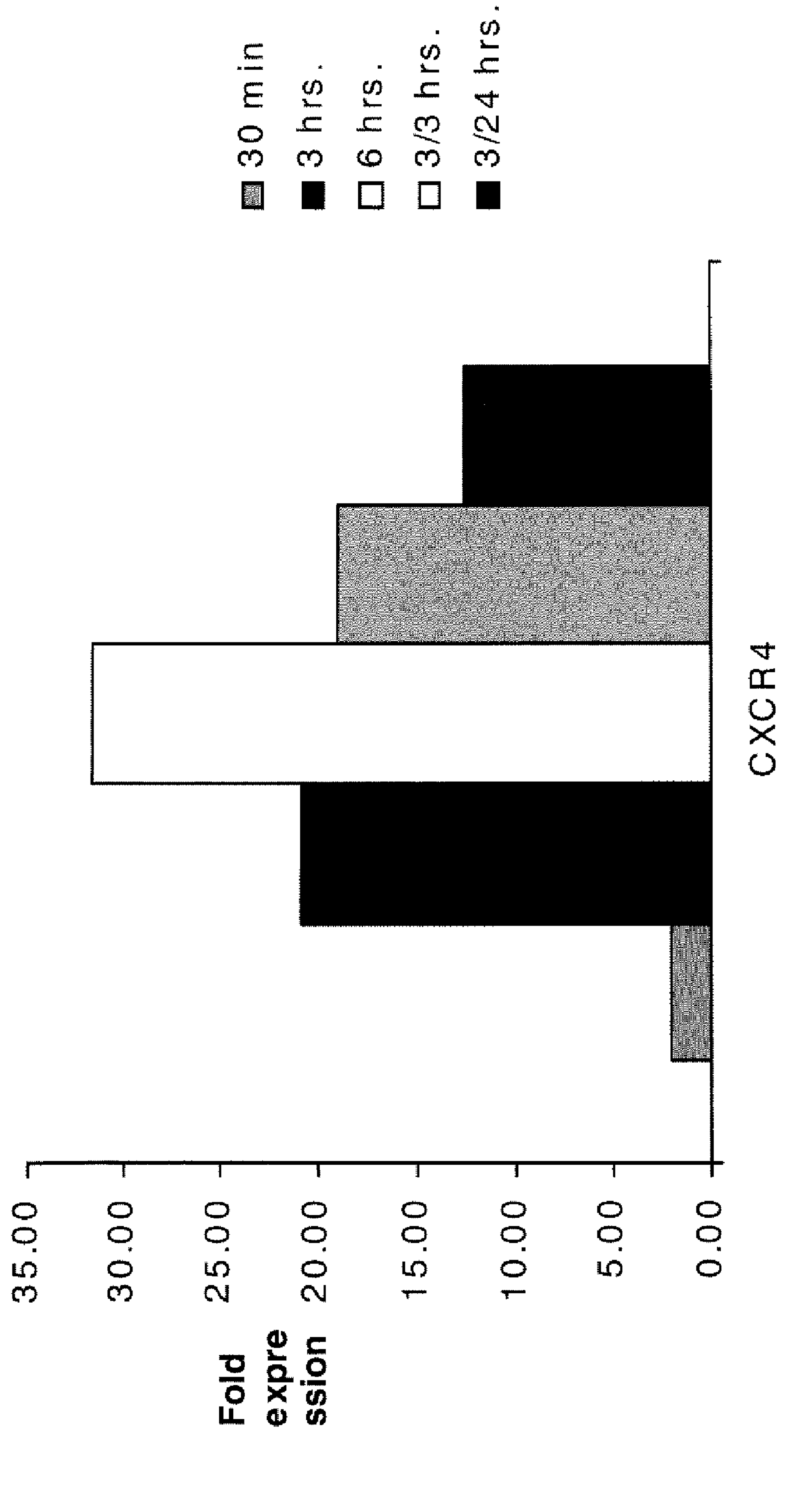
FIG. 1 shows the expression of CXCR4 mRNA in ARPE4-19 cells in fragmentation buffer.

We have discovered that RPE cells in which oxidative stress was induced displayed a significant increase in transcription of the CXCR4 gene, as judged from gene array analysis, when ARPE-19 cells were exposed to the chemical stressor (tertiary butyl hydroperoxide or t-BH) for 6 hours, experienced cell death within 24 hours. Cells exposed to the stressor for only 3 hours, by contrast, have a 70% survival rate of at least 24 hours. The degree of CXCR4 expression of these latter cells approached that of naive cells not exposed to the stressor at all.

Therefore, in one embodiment, the present invention is drawn to a method of reducing the rate of progression of an ophthalmic condition, such as an inflammatory retinal condition in a mammal, comprising: administering to the ophthalmic tissue of said mammal a composition comprising an inhibitor of CXCR4 activity.

In yet another embodiment the present invention is drawn to a method of inhibiting or reducing the rate of progression of retinal cell death (including RPE cell death), such as by apoptosis or necrosis, in inhibiting or reducing the rate of progression of apoptotic or necrotic retinal cell death in a mammal, comprising: administering to the retinal tissue of said mammal a composition comprising an inhibitor of CXCR4 activity.

In yet another embodiment the present invention is drawn to a method of inhibiting or reducing the rate of progression of retinal or choroidal angiogenesis in a mammal, comprising: administering to the retinal tissue of said mammal a composition comprising an inhibitor of CXCR4 activity. See. e.g., Tachibana et al., Nature 393:591 (June, 1998); Horuk, Nature 393:525 (June, 1998); Salcedo et al., Am. J. Pathology 154: 1125 (April, 1999); Kryczek et al., Cancer Res. 65:465 (Jan. 15, 2005); Zou et al., Nature 393:595 (June, 1998); Gupta et al., J. Biol. Chem. 273:4282 (Feb. 132 1998); Schioppa et al., J. Exp. Med. 198:1391 (Nov. 3, 2003). Additionally, the following references discuss the effects of SDF-1 on angiogenesis: Grunewald et al., Cell 124:174 (Jan. 13, 2006); Ruiz de Almodovar et al., Cell 124:174 (Jan. 13, 2006); Butler et al., J. Clin. Invest. 11586 (January 2005); Orimo et al., Cell 121:335 (May 6, 2005). All these references are hereby incorporated by reference herein.

Additionally, CXCR4 (along with CCR5) has been implicated in the etiology of infection of macrophages and T-cells by human immunodeficiency virus (HIV). Accordingly, has been the subject of much study. The following references, each of which is incorporated by reference herein in its entirety, disclose agents capable of inhibiting either or both the activity and the expression of CXCR4:

Small Molecule CXCR4 Inhibitors:

By "small molecule" is meant a chemical compound other than a polynucleotide or polypeptide. CXCR4 inhibitory small molecules are disclosed in, among other sources, Bridger et al. U.S. Publication No. 2002/0077339 A1; Bridger et al. U.S. Publication No. 2002/0147192 A1; Tudan et al. U.S. Publication No. 2002/0156034 A1; Bridger et al. U.S. Publication No. 2003/0220341 A1; Bridger et al. U.S. Pat. No. 6,667,320 B2; Bridger et al. U.S. Publication No. 2004/0019058 A1; Bridger et al. U.S. Publication No. 2004/0102428 A1; Yanaka et al. U.S. Publication No. 2004/0157818; Kishimoto et al. U.S. Publication No. 2004/0209837 A1; Bridger et al. U.S. Publication No. 2004/0209921 A1; Bridger et al. U.S. Publication No. 2004/0235814 A1; Yamazaki et al. U.S. Publication No. 2004/0254221 A1; Bridger et al. U.S. Pat. No. 6,835,731 B2; Zlotnik et al. U.S. Publication No. 2005/0002939 A1; Bridger et al. U.S. Publication No. 2005/0026942 A1; Schols U.S. Pat. No. 6,872,714 B1; Bridger et al. U.S. Publication No. 2005/0154005 A1; Winchester et al. U.S. Publication No. 2005/0202005 A1; Kaplan et al. U.S. Publication No. 2005/0239898 A1; Hanai et al. U.S. Publication No. 2005/0276805 A1; Tudan et al. U.S. Publication No. 2006/0014682 A1; Shim et al. U.S. Publication No. 2006/0264451; Losordo et al. U.S. Publication No. 2006/0194776; and Ochiai et al. International Publicaiton No. WO 2006/090853.

For example, and without limitation, Bridger et al., U.S. 2002/0077339 (the '339 application), filed Dec. 15, 2000 discloses CXCR4-binding modulators (including antagonists) comprising heterocyclic compounds of the basic structure:

$$V—CR_2—Ar^1—CR_2NR—(CR_2)_x—Ar^2$$

including the pharmaceutically acceptable salts and protected forms thereof, wherein V is a substituted heterocycle compound of 9-24 members containing 2-4 optionally substituted amine nitrogen atoms spaced from each other by 2 or more optionally substituted carbon atoms, and which heterocycle may optionally comprise a fused aromatic or heteroaromatic ring, and wherein (a) said heterocycle contains at least one O or S, said O or S spaced from any adjacent heteroatom by at least 2 carbon atoms, and wherein said S is optionally oxidized or (b) at least one carbon atom in said ring is substituted by an electron-withdrawing substituent, or (c) both (a) and (b);

and wherein each R is independently H or a straight chain, branched or cyclic alkyl containing 1-6 carbon atoms; x is 0-4; $Ar^1$ is an unsubstituted or substituted aromatic or heteroaromatic moiety; and $Ar^2$ is an unsubstituted or substituted aromatic or heterocyclic group.

Representative examples of such compounds and methods of making these compounds are given in FIGS. 1-10 and Examples 1-8 of the 339' publication, which also discloses the compounds' use for inhibition of HIV infection, for the treatment of collagen-induced arthritis, and its involvement in tumor growth, atherosclerosis.

As another example, without limitation, other CXCR4 inhibiting compounds are disclosed in Bridger et al., U.S. Publication No. 2004/0102428 (the '428 publication), filed Apr. 12, 2004. These have a generic structure comprising the formula:

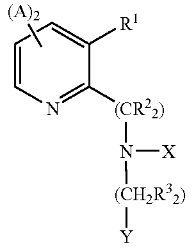

wherein X is $(CR^3{}_2)_o—(CR^3═CR^3)_p—(CR^3{}_2)_q—NR^5{}_2$; $(CR^3{}_2)_r—R^4$; a monocyclic or bicyclic ring optionally containing N, O or S; or a benzyl, each of which is optionally substituted; provided said benzyl is not substituted with a 5-6 membered aryl or heteroaryl via an L-NH-L linker, where each L is a bond, CO, $SO_2$ or $CH_2$; Y is an optionally substituted nitrogen-containing monocyclic or bicyclic aromatic or partially aromatic moiety; A and $R^1$ are each a non-interfering substituent, and provided that two As do not form an additional ring; $R^2$ and $R^3$ are independently H or an optionally substituted alkyl; $R^4$ is an optionally substituted heterocyclic ring; or a hetero compound containing at least one ═O, SO, C═N, cyano, NROR, or halo, wherein said hetero compound is optionally substituted with a heterocyclic ring; $R^5$ is H or alkyl; wherein at least one of $R^1$ and $R^2$ is not H; and wherein $R^1$ and $R^2$ may be connected to form an additional ring if Y does not contain a 2-imidazoyl residue optionally connected to an additional ring; l and n are independently 0-4; p is 0-1; o and q are independently 1-4; r is 1-6; provided that if X is $(CR^3{}_2)_r—R^4$, r is at least two if $R^4$ is 2-pyridinyl, quinolinyl, imidazolyl or furan; and further provided that said compound is not (1-pyridin-2-ethyl)-(2-pyridin- -2-yl-ethyl)-pyridin-2-ylmethyl-amine. Examples 1-441 of the '428 publication provide examples of specific compounds encompassed by this generic formula, and methods of making such compounds. This publication is incorporated by reference herein in its entirety.

Further, Yamazaki et al. U.S. Patent Publication No. 2004/0254221, filed Sep. 27, 2002 disclose other CXCR4 inhibitors of the following general formula (1) or a pharmacologically acceptable salt thereof:

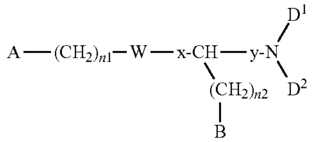

in the general formula (1), $n_1$ represents an integer of 0 to 3 and $n_2$ represents an integer of 0 to 4;

A represents a group represented b the following general formula (2):

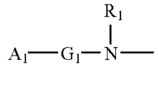

or

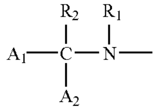

in the general formula (2), $A_1$ and $A_2$ each independently represent an optionally substituted mono- or polycyclic heteroaromatic ring, or an optionally substituted mono- or polycyclic aromatic ring;

$G_1$ represents a single bond or a group represented by the following general formula (3); and

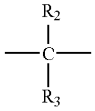

$R^1$, $R^2$ and $R^3$ represent a hydrogen atom, an optionally substituted alkyl group having 1 to 6 carbon atoms, an optionally substituted alkenyl group having 2 to 6 carbon atoms, an optionally substituted alkynyl group having 2 to 6 carbon atoms, or an optionally substituted cyclic alkyl group having 3 to 6 carbon atoms;

W represents an optionally substituted alkylene group having 1 to 7 carbon atoms, an optionally substituted alkenylene group having 2 to 7 carbon atoms, an optionally substituted alkynylene group having 2 to 7 carbon atoms, an optionally substituted cyclic alkylene group having 3 to 10 carbon atoms, an optionally substituted mono- or polycyclic aromatic ring, an optionally substituted mono- or polycyclic heteroaromatic ring, or an optionally substituted mono- or polycyclic saturated heterocyclic ring;

$D_1$ and $D_2$ each independently represent a hydrogen atom or a group represented by the following general formula (4):

$$-G_2-R_4 \qquad (4)$$

in the general formula (4), $G_2$ represents an optionally substituted alkylene group having 1 to 15 carbon atoms, an optionally substituted alkenylene group having 2 to 7 carbon atoms, or an optionally substituted alkynylene group having 2 to 7 carbon atoms; and $R_4$ represents a hydrogen atom, an optionally substituted cyclic alkyl group having 3 to 10 carbon atoms, an optionally substituted mono- or polycyclic aromatic ring, an optionally substituted and partly saturated polycyclic aromatic ring, an optionally substituted mono- or polycyclic heteroaromatic ring, an optionally substituted and partly saturated polycyclic heteroaromatic ring, or an optionally substituted mono- or polycyclic saturated heterocyclic ring;

B represents a group represented by the following general formula (5):

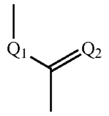

or

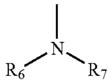

in the general formula (5), $Q_1$ represents S, O, or NH and $Q_2$ represents S, O, or $NR_8$ (except for a case of $Q_1$=NH and $Q_2$=$NR_8$); $R_5$ and $R_8$ each independently represent a hydrogen atom, an optionally substituted lower alkyl group, an optionally substituted cyclic alkyl group, or an optionally substituted aromatic ring, and $R_5$ and $R_8$ may optionally form a ring; and $R_6$ and $R_7$ each independently represent a hydrogen atom, a substituent represented by the following general formula (6), an optionally substituted alkyl group having 1 to 15 carbon atoms, an optionally substituted cyclic alkyl group having 3 to 15 carbon atoms, an optionally substituted alkenyl group having 1 to 3 double bonds and 2 to 15 carbon atoms, or an optionally substituted alkynyl group having 1 to 3 triple bonds and 2 to 15 carbon atoms, and $R_6$ and $R_7$ optionally form a ring, wherein $R_6$ and $R_7$ are optionally bonded with each other via a heteroatom, a cyclic alkyl group, an aromatic ring, a heteroaromatic ring, or a heterocyclic ring to form the ring:

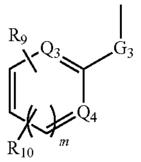

in the formula (6), m represents 0 or 1, when m=0, $Q_3$ represents CH or N and $Q_4$ represents N, S, or O, and when m=1, $Q_3$ and $Q_4$ each independently represent CH or N;

$G_3$ represents an optionally substituted alkylene group having 1 to 4 carbon atoms, or an optionally substituted alkenylene group having 2 to 4 carbon atoms;

$R_9$ represents a lower alkyl group, an alkoxy group, a haloalkyl group, a haloalkoxy group, a hydroxyalkoxy group, a halogen atom, an amino group, an alkylamino group, a carboxyl group, an alkoxycarbonyl group, a carbamoyl group, an alkylcarbamoyl group, a saturated heterocyclic ring, or a heteroaromatic ring, which is substituted at any position in a ring other than that of a nitrogen atom optionally existing in the ring, and when m=1 and $Q_3$ and $Q_4$ simultaneously represent CH, $R_9$ optionally represents a hydrogen atom;

$R_{10}$ represents a hydrogen atom, or a same group as $R_5$, and optionally bonds with $G_3$ to form a ring;

x represents a group represented by the following general formula (7):

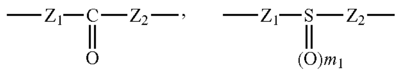

or

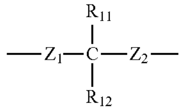

in the general formula (7), $z_1$ and $z_2$ each independently represent a single bond, S, O, or $NR_{13}$, and $m_1$ represents an integer of 1 or 2;

$R_{11}$, $R_{12}$, and $R_{13}$ each independently represent a hydrogen atom, an optionally substituted alkyl group having 1 to 6 carbon atoms, an optionally substituted alkenyl group having 2 to 6 carbon atoms, an optionally substituted alkynyl group having 2 to 6 carbon atoms, or an optionally substituted cyclic alkyl group having 3 to 6 carbon atoms; and y represents a group represented by the following general formula (8):

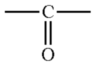

or

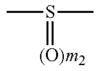

in the general formula (8), $m_2$ represents an integer of 1 or 2; and when there is one asymmetric carbon atom optionally existing in the compound represented by the general formula (1), the compound is in any form of a pure optical isomer represented as absolute configuration of R or S, a mixture thereof in any ratio, and a racemic mixture thereof, and when there are two or more of the asymmetric carbon atoms in the compound, the compound is in any form of an optically pure diastereomer, a racemic mixture thereof, and a combination thereof in any ratio.

Ochiai et al. disclose in WO 2006/090853, the contents of which are incorporated by reference, CXCR4 antagonists having the following general formula (9):

(I)

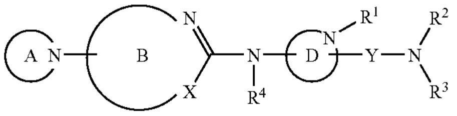

Ring A in this structure represents a 5-10 membered nitrogen-containing heterocyclic ring that may have a substituent; ring B represents a 5-10 membered unsaturated nitrogen-containing heterocyclic ring that may have a substituent; ring D represents a 4-15 membered nitrogen-containing heterocyclic ring that may have a substituent; X represents N or C; Y is $C_{1-6}$ substituted or unsubstituted alkyl; R1 represents H, a hydrocarbon group that may have a substituent, or a ring group that may have a substituent; R2 and R3 each independently represents H, a hydrocarbon group that may have a substituent, or a ring group that may have a substituent, or may form, together with nitrogen atom bonded to any of these, a nitrogen-containing heterocyclic ring that may have a substituent; and R4 represents H or a hydrocarbon group that may have a substituent.

In one embodiment of the CXCR4 antagonist of formula (9), the antagonist is a compound of formula (10):

(I-1)

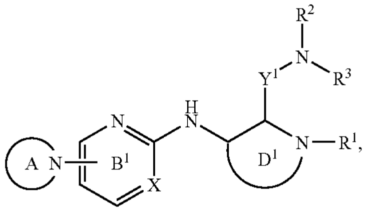

where ring B1 represents a pyridine or pyrimidine ring that may have a substituent; ring D1 represents a 4-8 membered saturated monocyclic nitrogen-containing heterocyclic ring that may have a substituent; Y1 represents a $C_{1-4}$ substituted or unsubstituted alkyl; and A, X, R1, R2, and R3 have the meanings given to them above.

In another embodiment of the compound of formula (10), Y1 is —(CR5R6)n-, wherein R5 and R6 each represents a hydrogen atom, or R5 and R6 together represent an oxo group; n represents a whole number between 1 and 4, and when n represents a whole number between 2 and 4 each of the CR5R6 may be identical or different.

In another embodiment of the compound of formula (10), R2 represents —(CO)— R2A, wherein R2A is (i) a hydrocarbon group that may be substituted by a basic group and may further have a substituent; (ii) a ring group that may be substituted by a basic group and may further have a substituent; or (iii) a 5-8 membered monocyclic nitrogen-containing heterocyclic ring, such as pyrrolidine, piperidine or morpholine; and R3 is a hydrocarbon group that may have a substituent or a ring group that may have a substituent.

In another embodiment of the compound of formula (10), the ring formed by R2 and R3 together with nitrogen atom(s) they bond to is a 5-8 membered nitrogen-containing heterocyclic ring that may have a substituent. In another embodiment of the compound of formula (10), D1 is pyrrolidine or piperidine.

In another embodiment of the CXCR4 antagonist of formula (9), the antagonist is a compound of formula (11):

(I-2)

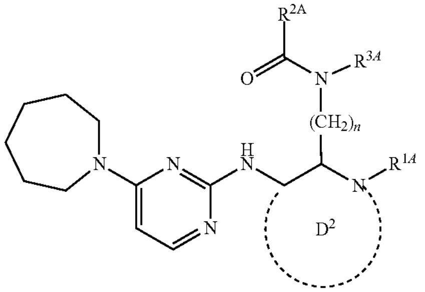

a compound of formula (12):

-continued (I-3)

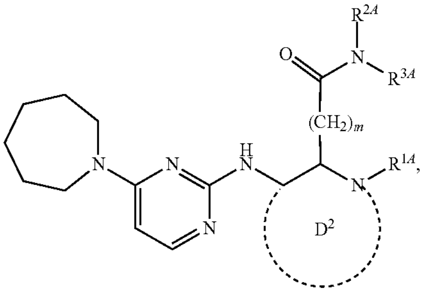

a compound of formula (13):

(I-4)

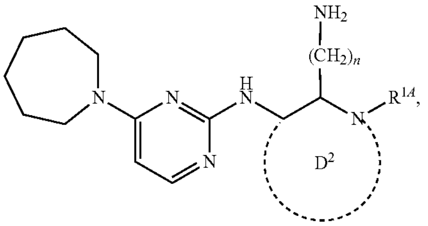

a compound of formula (14):

(I-5)

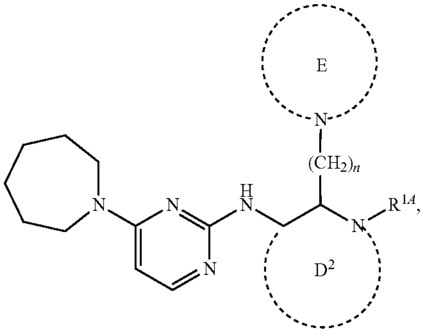

Wherein in each of formulas 11-14, the ring D2 represents pyrrolidine or piperidine; m represents a whole number between 1 and 3; R1A represents a hydrocarbon group that may have a substituent or a monocyclic ring group that may have a substituent; R3A represents a hydrocarbon group that may have a substituent or a ring group that may have a substituent; ring E represents a 5-8 membered monocyclic nitrogen-containing heterocycle that may have a substituent; and n represents a whole number between 1 and 4.

In another embodiment of the CXCR4 antagonist of formula (9), the antagonist is a compound of formula (15),

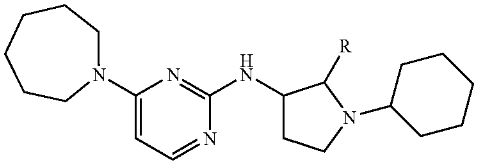

wherein R is $C_{1-6}$ alkyl-$NH_2$.

A substituent of alkyl, aryl, or heteroaryl should be stable and may have up to 20 non-hydrogen atoms each and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent is stable if it is sufficiently stable for the compound to be isolated for at least 12 hours at room temperature under normal atmospheric conditions, or if it is sufficiently stable to be useful for at least one use disclosed herein.

CXCR4 antagonists falling under the scope of one or more of formulas 9-15 include N-[(2R,3S)-2-(aminomethyl)-1-cyclohexyl-3-pyrrolidinyl]-4-(1-azepanyl)-2-pyrimidine amine, N-[(2R,3S)-2-(2-aminoethyl)-1-cyclohexyl-3-pyrrolidinyl]-4-(1-azepanyl)-2-pyrimidine amine, N-[(2R,3S)-2-(3-aminopropyl)-1-cyclohexyl-3-pyrrolidinyl]-4-(1-azepanyl)-2-pyrimidine amine, N-[(2R,3S)-2-(5-aminopentyl)-1-cyclohexyl-3-pyrrolidinyl]-4-(1-azepanyl)-2-pyrimidine amine, N-[(2R,3S)-2-(aminoethyl)-1-cyclohexyl-3-pyrrolidinyl]-4-(1-azepanyl)-2-pyrimidine amine, 4-(1-azepanyl)-N-{(2R,3S)-1-cyclohexyl-2-[2-(dimethylamino)ethyl]-3-pyrrolidinyl}-2-pyrimidine amine, 4-(1-azepanyl)-N-{(2R,3S)-1-cyclohexyl-2-[3-(dimethylamino)propyl]-3-pyrrolidinyl}-2-pyrimidine amine, 4-(1-azepanyl)-N-{(2R,3S)-1-cyclohexyl-2-[5-(dimethylamino)pentyl]-3-pyrrolidinyl}-2-pyrimidine amine, 4-(1-azepanyl)-N-{(2RS,3SR)-1-cyclohexyl-2-[3-(dipropylamino)propyl]-3-pyrrolidinyl}-2-pyrimidine amine, cis-4-((2RS,3SR)-2-(3-aminopropyl)-3-{[4-(1-azepanyl)-2-pyrimidinyl]amino}-1-pyrrolidinyl)cyclohexanol, 4-(1-azepanyl)-N-{(2RS,3SR)-1-cyclohexyl-2-[3-(diethylamino)propyl]-3-pyrrolidinyl}-2-pyrimidine amine, 4-(1-azepanyl)-N-{(2RS,3SR)-1-cyclohexyl-2-[3-(1-pyrrolidinyl)propyl]-3-pyrrolidinyl}-2-pyrimidine amine, 4-(1-azepanyl)-N-{(2RS,3SR)-1-cyclohexyl-2-[3-(1-piperidinyl)propyl]-3-pyrrolidinyl}-2-pyrimidine amine, 4-(1-azepanyl)-N-{(2RS,3SR)-2-[3-(1-azepanyl)propyl]-1-cyclohexyl-3-pyrrolidinyl}-2-pyrimidine amine, N-[(2RS,3SR)-2-(2-aminoethyl)-1-cyclohexyl-3-piperidinyl]-4-(1-azepanyl)-2-pyrimidine amine, N-{(2RS,3SR)-2-(3-aminopropyl)-1-[1-(cyclohexyl carbonyl)-4-piperidinyl]-3-pyrrolidinyl}-4-(1-azepanyl)-2-pyrimidine amine, N-{(2RS,3SR)-2-(3-aminopropyl)-1-[1-(cyclopentyl carbonyl)-4-piperidinyl]-3-pyrrolidinyl}-4-(1-azepanyl)-2-pyrimidine amine, N-{(2RS,3SR)-2-(3-aminopropyl)-1-[1-(3-fluorobenzoyl)-4-piperidinyl]-3-pyrrolidinyl}-4-(1-azepanyl)-2-pyrimidine amine, N-(3-aminopropyl)-2-((2RS,3SR)-3-{[4-(1-azepanyl)-2-pyrimidinyl]amino}-1-cyclohexyl-2-piperidinyl)acetamide, 2-((2RS,3SR)-3-{[4-(1-azepanyl)-2-pyrimidinyl]amino}-1-cyclohexyl-2-piperidinyl)-N-[3-(dimethylamino)propyl]acetamide, N-[2-((2RS,3SR)-3-{[4-(1-azepanyl)-2-pyrimidinyl]amino}-1-cyclohexyl-2-piperidinyl)ethyl]-4-piperidine carboxamide, cis-4-{(2RS,3SR)-3-{[4-(1-azepanyl)-2-pyrimidinyl]amino}-2-[3-(diethylamino)propyl]-1-pyrrolidinyl}cyclohexanol, N-{2-[(2RS,3SR)-3-{[4-(1-azepanyl)-2-pyrimidinyl]amino}-1'-(3-fluorobenzoyl)-1,4'-bipiperidine-2-yl)ethyl}-4-piperidine carboxamide, N-{2-[(2RS,3SR)-3-{[4-(1-azepanyl)-2-pyrimidinyl]amino}-1'-(cyclohexyl carbonyl)-1,4'-bipiperidine-2-yl)ethyl}-4-piperidine carboxamide, N-[2-((2RS,3SR)-3-{[4-(1-azepanyl)-2-pyrimidinyl]amino}-1-cyclohexyl-2-piperidinyl)ethyl]-2-morpholine carboxamide, (3S)-N-[2-((2RS,3SR)-3-{[4-(1-azepanyl)-2-pyrimidinyl]amino}-1-cyclohexyl-2-piperidinyl)ethyl]-3-piperidine carboxamide, (3R)-N-[2-((2RS,3SR)-3-{[4-(1-azepanyl)-2-pyrimidinyl] amino}-1-cyclohexyl-2-piperidinyl)ethyl]-3-piperidine carboxamide, (3R)-N-[2-((2RS,3SR)-3-{[4-(1-azepanyl)-2-pyrimidinyl]amino}-1-cyclohexyl-2-piperidinyl)ethyl]-3-pyrrolidine carboxamide, 2-amino-N-[2-((2RS,3SR)-3-{[4-(1-azepanyl)-2-pyrimidinyl]amino}-1-cyclohexyl-2-piperidinyl)ethyl]-2-methylpropanamide, N-(4- aminobutyl)-2-((2RS,3SR)-3-{[4-(1-azepanyl)-2-pyrimidinyl]amino}-1-cyclohexyl-2-piperidinyl)acetamide, N-(2-aminoethyl)-2-((2RS,3SR)-3-{[4-(1-azepanyl)-2-pyrimidinyl]amino}-1-cyclohexyl-2-piperidinyl)acetamide, (3S)—N-[2-((2RS,3SR)-3-{[4-(1-azepanyl)-2-pyrimidinyl]amino}-1-cyclohexyl-2-pyrrolidinyl)ethyl]-3-piperidine carboxamide, N-[2-((2RS,3SR)-3-{[4-(1-azepanyl)-2-pyrimidinyl]amino}-1-cyclohexyl-2-pyrrolidinyl)ethyl]-2-morpholine carboxamide, N-[2-((2RS,3SR)-3-{[4-(1-azepanyl)-2-pyrimidinyl]amino}-1-cyclohexyl-2-piperidinyl)ethyl]-1-isopropyl-4-piperidine carboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-4-piperidine carboxamide, N-[2-((2RS,3SR)-3-{[4-(1-azepanyl)-2-pyrimidinyl]amino}-1-cyclohexyl-2-piperidinyl)ethyl]-N-(2-methoxyethyl)-4-piperidine carboxamide, N-[2-((2RS,3SR)-3-{[4-(1-azepanyl)-2-pyrimidinyl]amino}-1-cyclohexyl-2-piperidinyl)ethyl]-N-(2-hydroxyethyl)-4-piperidine carboxamide, (2S)—N-[2-((2RS,3SR)-3-{[4-(1-azepanyl)-2-pyrimidinyl]amino}-1-cyclohexyl-2-piperidinyl)ethyl]-2-piperidine carboxamide, N-[2-((2RS,3SR)-3-{[4-(1-azepanyl)-2-pyrimidinyl]amino}-1-cyclohexyl-2-piperidinyl)ethyl]-1-ethyl-4-piperidine carboxamide, N-[2-((2RS,3SR)-3-{[4-(1-azepanyl)-2-pyrimidinyl]amino}-1-cyclohexyl-2-piperidinyl)ethyl]-4-hydroxy-4-piperidine carboxamide, (2R)-2-amino-N-[2-((2RS,3SR)-3-{[4-(1-azepanyl)-2-pyrimidinyl]amino}-1-cyclohexyl-2-piperidinyl)ethyl]-3-(4-hydroxyphenyl)propanamide, (2S)-2-amino-N-[2-((2RS,3SR)-3-{[4-(1-azepanyl)-2-pyrimidinyl]amino}-1-cyclohexyl-2-piperidinyl)ethyl]-4-hydroxybutanamide, N-(2-aminoethyl)-N-[2-((2RS,3SR)-3-{[4-(1-azepanyl)-2-pyrimidinyl]amino}-1-cyclohexyl-2-piperidinyl)ethyl]-4-piperidine carboxamide, N-[2-((2RS,3SR)-3-{[4-(1-azepanyl)-2-pyrimidinyl]amino}-1-ethyl-2-piperidinyl)ethyl]-4-piperidine carboxamide, N-{2-[(2RS,3SR)-3-{[4-(1-azepanyl)-2-pyrimidinyl]amino}-1-(tetrahydro-2H-thiopyran-4-yl)2-piperidinyl]ethyl}-4-piperidine carboxamide, N-[2-((2RS,3SR)-3-{[4-(1-azepanyl)-2-pyrimidinyl]amino}-1-isopropyl-2-piperidinyl)ethyl]-4-piperidine carboxamide, N-(2-{(2RS,3SR)-3-{[4-(1-azepanyl)-2-pyrimidinyl]amino}-1-[2-hydroxy-1-(hydroxymethyl)ethyl]-2-piperidinyl}ethyl)-4-piperidine carboxamide, (2R)-2-amino-N-[2-((2RS,3SR)-3-{[4-(1-azepanyl)-2-pyrimidinyl]amino}-1-cyclohexyl-2-piperidinyl)ethyl]-3-(1H-imidazole-4-yl)propanamide, (2S)-2-amino-N-[2-((2RS,3SR)-3-{[4-(1-azepanyl)-2-pyrimidinyl]amino}-1-cyclohexyl-2-piperidinyl)ethyl]-3-(1H-imidazole-4-yl)propanamide, N-{2-[(2RS,3SR)-3-{[4-(1-azepanyl)-2-pyrimidinyl]amino}-1-(tetrahydro-2H-pyran-4-yl)-2-piperidinyl]ethyl}-4-piperidine carboxamide, N-[2-((2RS,3SR)-3-{[4-(1-azepanyl)-2-pyrimidinyl]amino}-1-cyclohexyl-2-piperidinyl)ethyl]-2-piperidine carboxamide, N-[2-((2RS,3SR)-3-{[4-(1-azepanyl)-2-pyrimidinyl]amino}-1-cyclohexyl-2-piperidinyl)ethyl]nicotinamide, N-[2-((2RS,3SR)-3-{[4-(1-azepanyl)-2-pyrimidinyl]amino}-1-cyclohexyl-2-piperidinyl)ethyl]isonicotiniamide, N-{2-[(2RS,3SR)-3-{[4-(1-azepanyl)-2-pyrimidinyl]amino}-1-(1-oxidotetrahydro-2H-thiopyran-4-yl)-2-piperidinyl]ethyl}-4-piperidine carboxamide, N-{2-[(2RS,3SR)-3-{[4-(1-azepanyl)-2-pyrimidinyl]amino}-1-(1,1-dioxidotetrahydro-2H-thiopyran-4-yl)-2-piperidinyl]ethyl}-4-piperidine carboxamide, N-[2-((2RS,3SR)-1-cyclohexyl-3-{[4-(1-pyrrolidinyl)-2-pyrimidinyl]amino}-2-piperidinyl)ethyl]-4-piperidine carboxamide, N-[2-((2RS,3SR)-3-{[4-(1-azepanyl)-2-pyrimidinyl]amino}-1-isopropyl-2-piperidinyl)ethyl]-1-ethyl-4-piperidine carboxamide, N-[2-((2RS,3SR)-1-ethyl-3-{[4-(1-piperidinyl)-2-pyrimidinyl]amino}-2-piperidinyl)ethyl]-4-piperidine carboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-2-morpholine carboxamide, N-{2-[(2RS,3SR)-3-{[4-(1-azepanyl)-2-pyrimidinyl]amino}-1-(3-hydroxypropyl)-2-piperidinyl]ethyl}-4-piperidine carboxamide, N-(2-(3-aminopropyl)-1-cyclohexylpyrrolidin-3-yl)-4-(azepan-1-yl)pyrimidin-2-amine, N-((2R,3S)-2-(3-aminopropyl)-1-cyclohexylpyrrolidin-3-yl)-4-(azepan-1-yl)pyrimidin-2-amine, and pharmaceutically acceptable salts thereof and prodrugs thereof.

It will be understood by those of ordinary skill in the art that the explicit examples provided here of compounds capable of binding to CXCR4 and capable of blocking the endogenous agonists of this receptor, such as SDF-1α, are not meant to be an exclusive or even representative listing of embodiments of the CXCR4-inhibitory compounds disclosed herein. In particular, those of skill in the art are aware that similarly detailed descriptions of other CXCR4 inhibitors may be made by following the guidelines contained in the references incorporated by reference herein.

Protein Inhibitors of CXCR4 Activity

Various peptide and polypeptide antagonists of CXCR4 activity have been described; these include, without limitation, at least a CXCR4-binding peptide domain derived from SDF-1, wherein the SDF-1 derivative does not have the CXCR4 stimulatory activity of wild-type SDF-1; and antibodies or antibody mimics (such as those described under the name Adnectins™).

Additional inhibitors of CXCR4 activity are disclosed in each of the following references, which are hereby incorporated herein by reference in their entirety and which provide full and detailed description of the peptides as well as how to make and use them. These references include Hoxie U.S. Pat. No. 5,994,515; Winchester et al. U.S. Publication No. 2002/0039993 A1; Devico et al. U.S. Pat. No. 6,399,078 B1; Lobo U.S. Publication No. 2003/0099645; Lobo U.S. Pat. No. 6,610,834 B1; Hua et al. U.S. Publication No. 2003/0165988 A1; Huang et al. U.S. Publication No. 2003/0220482 A1; Wang et al. U.S. Pat. No. 6,808,877 B2; Clark-Lewis et al. U.S. Pat. No. 6,875,738 B1; Clark-Lewis et al. U.S. Pat. No. 6,946,445 B1; Mueller et al. U.S. Pat. No. 6,949,243 B1; Lobo U.S. Publication No. 2005/0220787 A1; Martinez-Alonzo et al. U.S. Publication No. 2005/0221287 A1; Clark-Lewis et al. U.S. Publication No. 2005/0265969 A1; Plaksin et al. U.S. Publication No. 2005/0266009 A1; Mueller et al. U.S. Publication No. 2005/0271665 A1.

Nucleic Acid Inhibitors of CXCR4 Activity

Additionally, nucleic acid inhibitors of SDF-1 activity have been described, These nucleic acid-based inhibitors may function at either the receptor binding level or the gene expression and translational levels. The nucleic acid inhibitors of CXCR4 activity include, without limitations, nucleic acid enzymes (such as ribozymes), nucleic acid aptamers, antisense nucleic acids, and RNAi, such as siRNA. Certain specific embodiments of exemplary nucleic acid CXCR4 inhibitors are contained in the following references: lijima et al. U.S. Pat. No. 6,429,308 B1; Guerciolini et al. U.S. Publication No. 2005/0124569 A1; Eagles et al. U.S. Pat. No. 6,916,653 B2; Watson et al. U.S. Publication No. 2005/0202077 A1.

In the present specification a "retinal disorder" means an inflammatory, apoptotic, necrotic or angiogenic condition affecting the retina of the eye. Such a condition may involve other structures or tissues as well, including, without limitation, the choroid and retinal pigmented epithelium (RPE).

However, in other embodiments of the present invention the oligonucleotides and polypeptides of the present invention may be used in treatment of any appropriate ocular condition. As used herein, an "ocular condition" is a disease, ailment or condition which affects or involves the eye or one of the parts or regions of the eye. Broadly speaking, the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

In yet another embodiment the present invention is drawn to compositions for use in the methods described above, and the use of such compositions.

To "treat," as used here, means to deal with medically. It includes administering inhibitors of CXCR4 activity to cure, mitigate, or prevent a condition. It will be understood that an "inhibitor of CXCR4 activity" or a "CXCR4 inhibitor" means an agent capable of blocking or otherwise preventing the generation or propagation of an intracellular CXCR4-selective signal that would, but for the presence of said agent, be capable of being generated or propagated under physiological conditions. Thus, such an inhibitor may comprise, without limitation, an antagonist of the CXCR4 receptor or of CXCR gene expression, a compound or complex able to bind SDF-1 and therefore to prevent and hinder SDF-1 from activating the CXCR4 receptor, or an agent able to reduce SDF-1 gene expression.

Such agents may comprise, for example and without limitation, peptide or oligonucleotide macromolecular components. The term "peptide" or polypeptide means a compound that may include a chain of two or more modified or non-modified naturally occurring or non-naturally occurring amino acids linked by at least one peptide bond. A peptide according to the present invention may also consist of, consist essentially of, or comprise a peptidomimetic. As used herein, the term "peptidomimetic" is used broadly to mean a peptide-like molecule that is able to serve as a model for a peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines (see, for example, Goodman and Ro, *Peptidomimetics for Drug Design*, in BURGER'S MEDICINAL CHEMISTRY AND DRUG DISCOVERY Vol. 1 (ed. M. E. Wolff; John Wiley & Sons 1995), pages 803-861), all volumes of which are hereby incorporated by reference herein.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an Nα-Cα cyclized amino acid; an Nα-methylated amino acid; a β- or γ-amino cycloalkane carboxylic acid; an α,β-unsaturated amino acid; a β,β-dimethyl or β-methyl amino acid; a β-substituted-2,3-methano amino acid; an NCδ or Cα-Cδ cyclized amino acid; or a substituted proline or another amino acid mimetic.

In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetic components are encompassed within the meaning of the term "peptidomimetic" as used herein. The term "polypeptide" or "peptide" shall include peptidomimetics unless expressly indicated otherwise. Furthermore, a protein or polypeptide according to the present invention shall be understood to consist of, consist essentially of, or comprise one or more peptide.

An "oligonucleotide" or "nucleic acid" according to the present invention may comprise two or more naturally occurring or non-naturally occurring deoxyribonucleotides or ribonucleotides linked by a phosphodiester linkage, or by a linkage that mimics a phosphodiester linkage to a therapeutically useful degree. According to the present invention, an oligonucleotide will normally be considered to be single-stranded unless stated to the contrary or otherwise obvious from the context, and a nucleic acid may be single stranded or double stranded. Additionally, an oligonucleotide or nucleic acid may contain one or more modified nucleotide; such modification may be made in order to improve the nuclease resistance of the oligonucleotide, to improve the hybridization ability (e.g., raise the melting temperature or Tm) of the resulting oligonucleotide, to aid in the targeting or immobilization of the oligonucleotide or nucleic acid, for a mixture of such purposes, or for some other purpose.

Such modifications may include oligonucleotide derivatives having modifications at the nitrogenous base, including replacement of the amino group at the 6 position of adenosine by hydrogen to yield purine; substitution of the 6-keto oxygen of guanosine with hydrogen to yield 2-amino purine, or with sulphur to yield 6-thioguanosine, and replacement of the 4-keto oxygen of thymidine with either sulphur or hydrogen to yield, respectively, 4-thiothymidine or 4-hydrothymidine. All these nucleotide analogues can be used as reactants for the synthesis of oligonucleotides. Other substituted bases are known in the art. See, e.g., Cook et al., International Publication No. WO 92/02258, entitled "Nuclease Resistant, Pyrimidine Modified Oligonucleotides that Detect and Modulate Gene Expression," which is hereby incorporated by reference herein. Base-modified nucleotide derivatives can be commercially obtained for oligonucleotide synthesis.

Similarly, a number of nucleotide derivatives have been reported having modifications of the ribofuranosyl or deoxyribofuranosyl moiety. See, e.g., Cook et al., International Publication No. WO 94/19023, entitled "Cyclobutyl Antisense Oligonucleotides, Methods of Making and Use Thereof"; McGee et al., International Publication No. WO 94/02501, entitled "Novel 2'-O-Alkyl Nucleosides and Phosphoramidites Processes for the Preparation and Uses Thereof"; and Cook, International Publication No. WO 93/13121, entitled "Gapped 2'-Modified Oligonucleotides." For example, 2'amino, 2'-C-allyl, 2'-fluoro, 2'-O-methyl, and 2'H groups tend to confer nuclease resistance and to permit hybridization between the modified nucleotide and an unaltered nucleotide in the annealed strand. Each of these publications is hereby incorporated by reference herein.

Most oligonucleotides comprising such modified bases have been formulated with increased cellular uptake, nuclease resistance, and/or increased substrate binding in mind. In other words, such oligonucleotides are described as therapeutic gene-modulating agents.

Nucleic acids having modified nucleotide residues exist in nature. Thus, depending on the type or source, modified bases in RNA can include methylated or dimethylated bases, deaminated bases, carboxylated bases, thiolated bases and bases having various combinations of these modifications. Additionally, 2'-O-alkylated bases are known to be present in naturally occurring nucleic acids. See e.g., Adams et al., The Biochemistry of the Nucleic Acids ($11^{th}$ ed 1992), hereby incorporated by reference herein.

CXCR4 Amino Acid and Nucleotide Sequences

The following disclosure is not intended to be an exclusive listing of peptide or nucleic acid CXCR4 forms or their inhibitors, but is provided to augment the disclosure provided elsewhere in this specification, such as, for example, in publications incorporated by reference as part of this disclosure.

Human CXCR4 amino acid sequences have been determined and are a matter of public record. Human CXCR4 amino acid sequences have been determined and is a matter of public record. The following human CXCR4 sequence has NCBI accession number P61073. All amino acid sequences shown are from N terminus to C terminus, and all nucleotide sequences shown are from 5' to 3', unless otherwise indicated.

```
                                               SEQ ID NO: 1
megisiytsd nyteemgsgd ydsmkepcfr eenanfnkif

lptiysiifl tgivgnglvi lvmgyqkklr smtdkyrlhl

svadllfvit lpfwavdava nwyfgnflck avhviytvnl

yssvlilafi sldrylaivh atnsqrprkl laekvvyvgv

wipallltip dfifanvsea ddryicdrfy pndlwvvvfq

fqhimvglil pgivilscyc iiisklshsk ghqkrkalkt

tvililaffa cwlpyyigis idsfilleii kqgcefentv

hkwisiteal affhcclnpi lyaflgakfk tsaqhaltsv

srgsslkils kgkrgghssv stesesssfh ss
```

Human CXCR4 cDNA sequences are as follows.

CXCR4 cDNA—Variant 1:

```
                                               SEQ ID NO: 2
tttttttct tccctctagt gggcggggca gaggagttag

ccaagatgtg actttgaaac cctcagcgtc tcagtgccct

tttgttctaa acaaagaatt ttgtaattgg ttctaccaaa

gaaggatata atgaagtcac tatgggaaaa gatggggagg

agagttgtag gattctacat taattctctt gtgcccttag

cccactactt cagaatttcc tgaagaaagc aagcctgaat

tggtttttta aattgcttta aaaatttttt ttaactgggt

taatgcttgc tgaattggaa gtgaatgtcc attcctttgc

ctcttttgca gatatacact tcagataact acaccgagga

aatgggctca ggggactatg actccatgaa ggaaccctgt

ttccgtgaag aaaatgctaa tttcaataaa atcttcctgc

ccaccatcta ctccatcatc ttcttaactg gcattgtggg

caatggattg gtcatcctgg tcatgggtta ccagaagaaa

ctgagaagca tgacggacaa gtacaggctg cacctgtcag

tggccgacct cctctttgtc atcacgcttc ccttctgggc

agttgatgcc gtggcaaact ggtactttgg gaacttccta

tgcaaggcag tccatgtcat ctacacagtc aacctctaca

gcagtgtcct catcctggcc ttcatcagtc tggaccgcta

cctggccatc gtccacgcca ccaacagtca gaggccaagg

aagctgttgg ctgaaaaggt ggtctatgtt ggcgtctgga
```

-continued

```
tccctgccct cctgctgact attcccgact tcatctttgc
caacgtcagt gaggcagatg acagatatat ctgtgaccgc
ttctacccca atgacttgtg ggtggttgtg ttccagtttc
agcacatcat ggttggcctt atcctgcctg gtattgtcat
cctgtcctgc tattgcatta tcatctccaa gctgtcacac
tccaagggcc accagaagcg caaggccctc aagaccacag
tcatcctcat cctggctttc ttcgcctgtt ggctgcctta
ctacattggg atcagcatcg actccttcat cctcctggaa
atcatcaagc aagggtgtga gtttgagaac actgtgcaca
agtggatttc catcaccgag gccctagctt tcttccactg
ttgtctgaac cccatcctct atgctttcct tggagccaaa
tttaaaacct ctgcccagca cgcactcacc tctgtgagca
gagggtccag cctcaagatc ctctccaaag gaaagcgagg
tggacattca tctgtttcca ctgagtctga gtcttcaagt
tttcactcca gctaacacag atgtaaaaga ctttttttta
tacgataaat aacttttttt taagttacac atttttcaga
tataaaagac tgaccaatat tgtacagttt ttattgcttg
ttggattttt gtcttgtgtt tctttagttt ttgtgaagtt
taattgactt atttatataa attttttttg tttcatattg
atgtgtgtct aggcaggacc tgtggccaag ttcttagttg
ctgtatgtct cgtggtagga ctgtagaaaa gggaactgaa
cattccagag cgtgtagtga atcacgtaaa gctagaaatg
atccccagct gtttatgcat agataatctc tccattcccg
tggaacgttt ttcctgttct taagacgtga ttttgctgta
gaagatggca cttataacca aagcccaaag tggtatagaa
atgctggttt ttcagttttc aggagtgggt tgatttcagc
acctacagtg tacagtcttg tattaagttg ttaataaaag
tacatgttaa acttaaaaaa aaaaaaaaaa aa
```

Genbank Accession Number MN_001008540 (Dec. 9, 2005).

This cDNA encodes a CXCR4 protein having a longer amino acid sequence than the CXCR4 shown in SEQ ID No: 1. In frame (+2) start codons are found at positions 131 and 152, with a stop codon at position 220. An additional start codon is found at position 305, at which point the nucleotide sequence remains identical with that of SEQ ID No. 3, shown below, which encodes SEQ ID No. 1. Other in-frame start codons are found at positions 362, 386, 506, 530, and 929. The presently preferred stop codon in this portion of the frame is located at position 1372. Given these features, a genus of possible isoforms are disclosed and suggested by this disclosure, having various 5' termini but with each with a C terminus ending in the amino acids SSFHSS.

Human CXCR4 cDNA—Variant 2:

In this CXCR4 variant sequence, the ATG start codon encoding SEQ ID NO: 1 begins at residue 96 and proceeds to residue 1151. The 5' untranslated region and N terminus of the translated protein are different from that of the DNA sequence of, and respective protein encoded by, SEQ ID No: 2, but beginning with residue 6 of the protein encoded by this cDNA (corresponding to nucleotide residue 108), the amino acid sequences are again identical.

SEQ ID NO: 3

```
aacttcagtt tgttggctgc ggcagcaggt agcaaagtga
cgccgagggc ctgagtgctc cagtagccac cgcatctgga
gaaccagcgg ttaccatgga ggggatcagt atatacactt
cagataacta caccgaggaa atgggctcag gggactatga
ctccatgaag gaaccctgtt tccgtgaaga aaatgctaat
ttcaataaaa tcttcctgcc caccatctac tccatcatct
tcttaactgg cattgtgggc aatggattgg tcatcctggt
catgggttac cagaagaaac tgagaagcat gacggacaag
tacaggctgc acctgtcagt ggccgacctc ctctttgtca
tcacgcttcc cttctgggca gttgatgccg tggcaaactg
gtactttggg aacttcctat gcaaggcagt ccatgtcatc
tacacagtca acctctacag cagtgtcctc atcctggcct
tcatcagtct ggaccgctac ctggccatcg tccacgccac
caacagtcag aggccaagga agctgttggc tgaaaaggtg
gtctatgttg gcgtctggat ccctgccctc ctgctgacta
ttcccgactt catctttgcc aacgtcagtg aggcagatga
cagatatatc tgtgaccgct tctaccccaa tgacttgtgg
gtggttgtgt tccagtttca gcacatcatg gttggcctta
tcctgcctgg tattgtcatc ctgtcctgct attgcattat
catctccaag ctgtcacact ccaagggcca ccagaagcgc
aaggccctca agaccacagt catcctcatc ctggctttct
tcgcctgttg gctgccttac tacattggga tcagcatcga
ctccttcatc ctcctggaaa tcatcaagca agggtgtgag
tttgagaaca ctgtgcacaa gtggatttcc atcaccgagg
ccctagcttt cttccactgt tgtctgaacc ccatcctcta
tgctttcctt ggagccaaat ttaaaacctc tgcccagcac
gcactcacct ctgtgagcag agggtccagc ctcaagatcc
tctccaaagg aaagcgaggt ggacattcat ctgtttccac
tgagtctgag tcttcaagtt ttcactccag ctaacacaga
tgtaaaagac ttttttttat acgataaata actttttttt
aagttacaca tttttcagat ataaaagact gaccaatatt
gtacagtttt tattgcttgt tggatttttg tcttgtgttt
ctttagtttt tgtgaagttt aattgactta tttatataaa
ttttttttgt ttcatattga tgtgtgtcta ggcaggacct
gtggccaagt tcttagttgc tgtatgtctc gtggtaggac
tgtagaaaag ggaactgaac attccagagc gtgtagtgaa
tcacgtaaag ctagaaatga tccccagctg tttatgcata
gataatctct ccattcccgt ggaacgtttt tcctgttctt
```

-continued

```
aagacgtgat tttgctgtag aagatggcac ttataaccaa
agcccaaagt ggtatagaaa tgctggtttt tcagttttca
ggagtgggtt gatttcagca cctacagtgt acagtcttgt
attaagttgt taataaaagt acatgttaaa cttaaaaaaa
aaaaaaaaaa a
```

Genbank Accession Number MN_003467 (Dec. 9, 2005).

As of Nov. 25, 2005 the National Center For Biotechnology Information (NCBI) maintained a publicly available NCBI internet catalog of 1125 entries of amino acid sequences collected from various species related to CXCR4. All CXCR4 and SDF-1 sequences listed therein are hereby incorporated by references herein.

SDF-1 Amino Acid and Nucleotide Sequences

In a number of reports the first residue of mature SDF-1 is the lysine residue, corresponding to position 21 of SEQ ID NO: 4, 5, and 6 of the following SDF-1 amino acid sequences. The following proline residue has been shown to be important for the activity of SDF-1, as a substitution of this reside with, for example, glycine preserves CXCR4 binding activity while converting SDF-1 into a CXCR4 antagonist. See also Crump et al., The EMBO J. 16:6996-7007 (1997), hereby incorporated by reference herein in its entirely.

Human SDF-1α

SEQ ID NO: 4

```
mnakvvvvlv lvltalclsd gkpvslsyrc pcrffeshva
ranvkhlkil ntpncalqiv arlknnnrqv cidpklkwiq
eylekalnk
```

NCBI accession number: NP_954637 (Nov. 25, 2005)

Human SDF-1β mnakvvvvlv lvltalclsd gkpvslsyrc pcrffeshva ranvkhlkil ntpncalqiv arlknnnrqv cidpklkwiq eylekalnkr fkm

SEQ ID NO: 5

NCBI accession number: NP_000600 (Nov. 25, 2005)

Human SDF-1γ

SEQ ID NO: 6

```
mnakvvvvlv lvltalclsd gkpvslsyrc pcrffeshva
ranvkhlkil ntpncalqiv arlknnnrqv cidpklkwiq
eylekalnkg rreekvgkke kigkkkrqkk rkaaqkrkn
```

NCBI accession number: NP_001029058 (Nov. 25, 2005)

SDF-1 cDNA Sequences

SDF-1 cDNA Variant 1 (SDF-1α)

SEQ ID NO: 7

```
gcactttcac tctccgtcag ccgcattgcc cgctcggcgt
ccggcccccg acccgcgctc gtccgcccgc ccgcccgccc
gcccgcgcca tgaacgccaa ggtcgtggtc gtgctggtcc
tcgtgctgac cgcgctctgc ctcagcgacg ggaagcccgt
cagcctgagc tacagatgcc catgccgatt cttcgaaagc
catgttgcca gagccaacgt caagcatctc aaaattctca
acactccaaa ctgtgccctt cagattgtag cccggctgaa
```

-continued

```
gaacaacaac agacaagtgt gcattgaccc gaagctaaag
tggattcagg agtacctgga gaaagcttta aacaagtaag
cacaacagcc aaaaaggact ttccgctaga cccactcgag
gaaaactaaa accttgtgag agatgaaagg gcaaagacgt
gggggagggg gccttaacca tgaggaccag gtgtgtgtgt
ggggtgggca cattgatctg ggatcgggcc tgaggtttgc
cagcatttag accctgcatt tatagcatac ggtatgatat
tgcagcttat attcatccat gccctgtacc tgtgcacgtt
ggaactttta ttactggggt ttttctaaga aagaaattgt
attatcaaca gcattttcaa gcagttagtt ccttcatgat
catcacaatc atcatcattc tcattctcat tttttaaatc
aacgagtact tcaagatctg aatttggctt gtttggagca
tctcctctgc tcccctgggg agtctgggca cagtcaggtg
gtggcttaac agggagctgg aaaaagtgtc ctttcttcag
acactgaggc tcccgcagca gcgcccctcc caagaggaag
gcctctgtgg cactcagata ccgactgggg ctgggcgccg
ccactgcctt cacctcctct ttcaacctca gtgattggct
ctgtgggctc catgtagaag ccactattac tgggactgtg
ctcagagacc cctctcccag ctattcctac tctctccccg
actccgagag catgcttaat cttgcttctg cttctcattt
ctgtagcctg atcagcgccg caccagccgg gaagagggtg
attgctgggg ctcgtgccct gcatccctct cctcccaggg
cctgccccac agctcgggcc ctctgtgaga tccgtctttg
gcctcctcca gaatggagct ggccctctcc tggggatgtg
taatggtccc cctgcttacc cgcaaaagac aagtctttac
agaatcaaat gcaattttaa atctgagagc tcgctttgag
tgactgggtt ttgtgattgc ctctgaagcc tatgtatgcc
atggaggcac taacaaactc tgaggtttcc gaaatcagaa
gcgaaaaaat cagtgaataa accatcatct tgccactacc
ccctcctgaa gccacagcag ggtttcaggt tccaatcaga
actgttggca aggtgacatt tccatgcata aatgcgatcc
acagaaggtc ctggtggtat ttgtaacttt ttgcaaggca
tttttttata tatattttg tgcacatttt tttttacgtt
tctttagaaa acaaatgtat ttcaaaatat atttatagtc
gaacaattca tatatttgaa gtggagccat atgaatgtca
gtagtttata cttctctatt atctcaaact actggcaatt
tgtaaagaaa tatatatgat atataaatgt gattgcagct
tttcaatgtt agccacagtg tatttttca cttgtactaa
aattgtatca aatgtgacat tatatgcact agcaataaaa
tgctaattgt ttcatggtat aaacgtccta ctgtatgtgg
```

-continued gaatttattt acctgaaata aaattcatta gttgttagtg atggagctta aaaaaaa

GenBank accession number MN-099068 (Dec. 9, 2005)
SDF-1 cDNA Variant 2 (SDF-1β)

SEQ ID NO: 1 megisiytsd nyteemgsgd ydsmkepcfr eenanfnkif lptiysiifl tgivgnglvi lvmgyqkklr smtdkyrlhl svadllfvit lpfwavdava nwyfgnflck avhviytvnl yssvlilafi sldrylaivh atnsqrprkl laekvvyvgv wipallltip dfifanvsea ddryicdrfy pndlwvvvfq fqhimvglil pgivilscyc iiisklshsk ghqkrkalkt tvililaffa cwlpyyigis idsfilleii kqgcefentv hkwisiteal affhcclnpi lyaflgakfk tsaqhaltsv srgsslkils kgkrgghssv stesesssfh ss

SEQ ID NO: 8 gcactttcac tctccgtcag ccgcattgcc cgctcggcgt ccggcccccg acccgcgctc gtccgcccgc ccgcccgccc gcccgcgcca tgaacgccaa ggtcgtggtc gtgctggtcc tcgtgctgac cgcgctctgc ctcagcgacg ggaagcccgt cagcctgagc tacagatgcc catgccgatt cttcgaaagc catgttgcca gagccaacgt caagcatctc aaaattctca acactccaaa ctgtgccctt cagattgtag cccggctgaa gaacaacaac agacaagtgt gcattgaccc gaagctaaag tggattcagg agtacctgga gaaagcttta aacaagaggt tcaagatgtg agagggtcag acgcctgagg aacccttaca gtaggagccc agctctgaaa ccagtgttag ggaagggcct gccacagcct cccctgccag ggcagggccc caggcattgc caagggcttt gttttgcaca ctttgccata ttttcaccat ttgattatgt agcaaaatac atgacattta tttttcattt agtttgatta ttcagtgtca ctggcgacac gtagcagctt agactaaggc cattattgta cttgccttat tagagtgtct ttccacggag ccactcctct gactcagggc tcctgggttt tgtattctct gagctgtgca ggtggggaga ctgggctgag ggagcctggc cccatggtca gccctagggt ggagagccac caagagggac gcctgggggt gccaggacca gtcaacctgg gcaaagccta gtgaaggctt ctctctgtgg gatgggatgg tggagggcca catgggaggc tcaccccctt ctccatccac atgggagccg ggtctgcctc ttctgggagg gcagcagggc taccctgagc tgaggcagca gtgtgaggcc agggcagagt gagacccagc cctcatcccg agcacctcca catcctccac gttctgctca tcattctctg tctcatccat catcatgtgt -continued gtccacgact gtctccatgg ccccgcaaaa ggactctcag gaccaaagct ttcatgtaaa ctgtgcacca agcaggaaat gaaaatgtct tgtgttacct gaaaacactg tgcacatctg tgtcttgttt ggaatattgt ccattgtcca atcctatgtt tttgttcaaa gccagcgtcc tcctctgtga ccaatgtctt gatgcatgca ctgttccccc tgtgcagccg ctgagcgagg agatgctcct tgggcccttt gagtgcagtc ctgatcagag ccgtggtcct ttggggtgaa ctaccttggt tcccccactg atcacaaaaa catggtgggt ccatgggcag agcccaaggg aattcggtgt gcaccagggt tgaccccaga ggattgctgc cccatcagtg ctccctcaca tgtcagtacc ttcaaactag ggccaagccc agcactgctt gaggaaaaca agcattcaca acttgttttt ggtttttaaa acccagtcca caaaataacc aatcctggac atgaagattc tttcccaatt cacatctaac ctcatcttct tcaccatttg gcaatgccat catctcctgc cttcctcctg ggccctctct gctctgcgtg tcacctgtgc ttcgggccct tcccacagga catttctcta agagaacaat gtgctatgtg aagagtaagt caacctgcct gacatttgga gtgttcccct tccactgagg gcagtcgata gagctgtatt aagccactta aaatgttcac ttttgacaaa ggcaagcact tgtgggtttt tgttttgttt ttcattcagt cttacgaata cttttgccct ttgattaaag actccagtta aaaaaaattt taatgaagaa agtggaaaac aaggaagtca aagcaaggaa actatgtaac atgtaggaag taggaagtaa attatagtga tgtaatcttg aattgtaact gttcttgaat ttaataatct gtagggtaat tagtaacatg tgttaagtat tttcataagt atttcaaatt ggagcttcat ggcagaaggc aaacccatca acaaaaattg tcccttaaac aaaaattaaa atcctcaatc cagctatgtt atattgaaaa aatagagcct gagggatctt tactagttat aaagatacag aactctttca aaaccttttg aaattaacct ctcactatac cagtataatt gagttttcag tggggcagtc attatccagg taatccaaga tattttaaaa tctgtcacgt agaacttgga tgtacctgcc cccaatccat gaaccaagac cattgaattc ttggttgagg aaacaaacat gaccctaaat cttgactaca gtcaggaaag gaatcatttc tatttctcct ccatgggaga aaatagataa gagtagaaac tgcagggaaa attatttgca taacaattcc tctactaaca atcagctcct tcctggagac tgcccagcta aagcaatatg catttaaata cagtcttcca tttgcaaggg aaaagtctct tgtaatccga atctcttttt gctttcgaac tgctagtcaa gtgcgtccac gagctgttta ctagggatcc ctcatctgtc -continued

```
cctccgggac ctggtgctgc ctctacctga cactcccttg
ggctccctgt aacctcttca gaggccctcg ctgccagctc
tgtatcagga cccagaggaa ggggccagag gctcgttgac
tggctgtgtg ttgggattga gtctgtgcca cgtgtttgtg
ctgtggtgtg tccccctctg tccaggcact gagataccag
cgaggaggct ccagagggca ctctgcttgt tattagagat
tacctcctga gaaaaaaggt tccgcttgga gcagaggggc
tgaatagcag aaggttgcac ctcccccaac cttagatgtt
ctaagtcttt ccattggatc tcattggacc cttccatggt
gtgatcgtct gactggtgtt atcaccgtgg gctccctgac
tgggagttga tcgcctttcc caggtgctac acccttttcc
agctggatga gaatttgagt gctctgatcc ctctacagag
cttccctgac tcattctgaa ggagccccat tcctgggaaa
tattccctag aaacttccaa atcccctaag cagaccactg
ataaaaccat gtagaaaatt tgttattttg caacctcgct
ggactctcag tctctgagca gtgaatgatt cagtgttaaa
tgtgatgaat actgtatttt gtattgtttc aattgcatct
cccagataat gtgaaaatgg tccaggagaa ggccaattcc
tatacgcagc gtgctttaaa aaataaataa gaaacaactc
tttgagaaac aacaatttct actttgaagt cataccaatg
aaaaaatgta tatgcactta taattttcct aataaagttc
tgtactcaaa tgtagccacc aa
```

GenBank accession number MN_000609 (Dec. 9, 2005) SDF-1 cDNA Variant 3

SEQ ID NO: 9

```
gcactttcac tctccgtcag ccgcattgcc cgctcggcgt
ccggcccccg acccgcgctc gtccgcccgc ccgcccgccc
gcccgcgcca tgaacgccaa ggtcgtggtc gtgctggtcc
tcgtgctgac cgcgctctgc ctcagcgacg ggaagcccgt
cagcctgagc tacagatgcc catgccgatt cttcgaaagc
catgttgcca gagccaacgt caagcatctc aaaattctca
acactccaaa ctgtgccctt cagattgtag cccggctgaa
gaacaacaac agacaagtgt gcattgaccc gaagctaaag
tggattcagg agtacctgga gaaagcttta aacaaggggc
gcagagaaga aaaagtgggg aaaaaaagaaa agataggaaa
aaagaagcga cagaagaaga gaaaggctgc ccagaaaagg
aaaaactagt tatctgccac ctcgagatgg a
```

GenBank accession number MN-001033886 (Dec. 9, 2005)

Translation of SDF-1 from SEQ ID NO: 2 and SEQ ID NO: 3, and comparison of the resulting peptides shows that while the majority of the two peptides are identical (up to residue 89 of the SDR-1 peptide), the C-termini of the two peptides vary, with the peptide translated from Variant 2 being 93 amino acids in length and the peptide translated from Variant 3 being 119 amino acids in length. The peptide resulting from Variant 1 is identical to these two peptides along the same region of identity, but terminates at residue 89.

Those of skill in the art will recognize that since the first 89 amino acids of SEQ ID NO: 4, 5, and 6 are identical, the design of certain inhibitors, such as for example, RNAi inhibitors, of the SDF-1 isoforms would be routine in light of the disclosure of the present specification.

Those of skill in the art also are aware that inhibitors can be directed in whole or in part to the 5' and 3' untranslated regions (UTRs) of one or more cDNA variant. It is commonly known that RNAi and antisense oligonucleotides are capable of inhibiting translation of mRNA in the coding region, in the 5' UTR and in the 3' UTR, and RNAi templates may be made that are complementary to these regions, or to regions bridging two such regions. Of course, more than one RNAi template may be used, with various loci in the mRNA being targeted for RNA-induced mRNA digestion and inhibition of translation.

Those of skill in the art will recognize that disclosure of the amino acid sequences herein also provides explicit written description of each and every nucleotide sequence that encodes these amino acid sequences. Moreover, those of skill in the art recognize that it is now a matter of routine for the person of skill in the art to obtain a nucleic acid using codons selected for optimal expression in a given host in order to optimize the production of such sequences.

Polypeptide CXCR4 Inhibitors

Polypeptide inhibitors of CXCR4 activity may include peptides, polypeptides, and proteins. In particularly preferred embodiments of the invention, the therapeutic agent may comprise a protein, a modified SDF-1 derivative comprising a CXCR4 binding region (but lacking CXCR4 stimulatory activity) a polyclonal or monoclonal antibody, an antibody fragment, such as, without limitation, a monovalent fraction antigen-binding papain fragment (Fab) or a bivalent fraction antigen binding pepsin fragment (F'ab$_2$). Additionally, the antibodies or antibody fragments may be naturally occurring or genetically engineered.

For example, the term "antibodies" may include chimeric antibodies comprising human $L_C$ and $H_C$ regions and $L_V$ and $H_V$ regions from another species, for example, from mouse, goat, rabbit or sheep cells. Preferably the non-human species is a mouse. Chimeric antibodies are useful in the design of antibody-based drugs, since the use of unaltered mouse antibodies induces the production of human anti-mouse immunoglobulins and resultant clearance and reduction of efficacy.

However, chimeric antibodies, while having reduced immunogenicity as compared to the rodent antibody, do not solve all the problems that exist in the use of antibodies as drugs. For example, to minimize allotypic variation in the constant regions a human consensus sequence can be used representing the most common allotype in the general population. A further refinement has been used, called complimentarily determining region (CDR) grafting. In this method, only the three antigen biding sites (formed by the three CDRs of the heavy chain and the three CDRs of the light chain) are excised from the murine antibodies and the nucleic acid regions encoding these CDRs have been inserted (or "grafted") into a nucleic acid coding sequence encoding the framework region of the human antibody.

Further refinements may comprise what has been termed "reshaping", "veneering" and "hyperchimerization". In reshaping, the rodent variable region is compared with the consensus sequence of the protein sequence subgroup to which it belongs, as is the human framework compared with a consensus of the framework sequence for the antibody family to which it belongs. This analysis can identify amino acid residues that may be the result of mutation during the affinity maturation process; these residues are called "idiosyncratic". By incorporating the more common human residues in these positions, immunogenicity problems resulting from the idiosyncratic residues can be minimized.

Humanization by hyperchimerization involves a comparison of the human and murine non-CDR variable region sequences and the one with the highest homology is selected as the acceptor framework. Again, idiosyncratic residues are replaced with more highly conserved human ones. Those non-CDR residues that may interact with the CDR residues are identified and inserted into the framework sequence.

Veneering involves determining the three dimensional conformation of a humanized murine antibody and replacing the expose surface amino acids with those commonly found in human antibodies. In the first step the most homologous human variable regions are selected and compared to the corresponding mouse variable regions. In the second step, the mouse framework residues differing from the human framework are replaced with the human residues; only those residues fully or partially exposed at the surface of the antibody are changed.

In the present case the desired inhibitor may be directed to bind, for example, an SDF-1 molecule or a CXCR4 receptor molecule. In the first case, an anti-SDF-1 binding polypeptide, when permitted to contact SDF-1 in a tissue or cell will prevent the SDF-1 molecule from activating a CXCR4 receptor in such tissue or cell. Otherwise the inhibitor may be an anti-CXCR4 polypeptide, such as a CXCR4 antagonist or inverse agonist.

An example of such an inhibitor may be, for example, the anti-CXCL12/SDF-1β antibody sold by R&D Systems (614 McKinley Place NE, □Minneapolis, Minn. 55413) under catalog number AF-351-NA and described as a goat anti-human CXCL12/SDF-1β IgG. This polyclonal antibody preparation was prepared in goats immunized with purified, *E. coli* derived, recombinant human CXCL12/SDF-1β. This antibody was first purified by passing the goat sera over an SDF-1α affinity column, and then the unbound fraction was further purified by binding to an SDF-1β affinity column.

This antibody preparation has a neutralization dose ($ND_{50}$) (that concentration required to yield ½ maximal inhibition of the cytokine activity in a responsive cell line, when that cytokine is present at a concentration just high enough to elicit a maximum response) of approximately 10-30 μg/ml in the presence of 10 ng/ml CXCL12, as assay measuring chemotaxis of BaF/3 cells transfected with human CXCR4.

Furthermore, as explained above, it is now routine to use various methods, including without exception computer modeling methods, to construct humanized antibodies derived originally from, for example, goat, rat, mouse, or rabbit antibodies. The variable region of antibodies having greater than a threshold level of avidity for the CXCR4 or SDF-1 mRNA can be sequenced and used to provide the basis for a therapeutic antibody or antibody derivative. See e.g., Hodxie et al., U.S. Pat. No. 5,994,515 (disclosing antibodies directed towards CXCR4); Mueller et al, U.S. Pat. No. 6,949, 243 (disclosing antibody preparations having anti-CXCR4 and anti SDF-1 activity); Plaskin et Al., U.S. Patent Publication No. 2005/0266009 (disclosing antibodies directed against CXCR4.)

SDF-1 derivatives lacking CXCR4 stimulatory activity have been disclosed in, e.g., Clark-Lewis et al., U.S. Pat. No. 6,875,738 (disclosing CXCR4-inhibitory derivatives of SDF-1α and SDF-1β. Huang et al., U.S. Publication No. 2003/0220482 discloses anti-CXCR4 peptides derived from viral HHV8 (human herpes virus 8) Macrophage Inflammatory Protein II.

Additional CXCR4 inhibitors are known in the art. Examples are described, for example, in Tudan, et al. U.S. Publication No. 2006/0014682; Clark-Lewis et al. U.S. Publication No. 2005/0265969.

Nucleic Acid CXCR4 Inhibitors

Inhibitors of CXCR4 activity may also comprise compositions containing a nucleic acid component. Such nucleic acids may include without exception RNAi molecules, such as dsRNA and siRNA.

Inhibitory nucleic acids may comprise, for example, a single-stranded oligonucleotide sufficiently complementary to a region of a target mRNA such that said oligonucleotide prevents translation of said mRNA. In certain embodiments said region comprises the 5' UTR, the ribosome binding site of said mRNA, the coding region of said mRNA, and may include the 5'start codon of said mRNA. Other targets may include the 3' UTR Said oligonucleotide may comprise one or more modified nucleotide residue (such as, without limitation, a 2'O alkyl nucleotide); preferably said modified nucleotide residue confers at least one of a nuclease resistance or a higher binding avidity. It will be understood that as used here an oligonucleotide may comprise a peptide nucleic acid, or other nucleic acid mimic. According to one aspect of the present invention, the target mRNA may be a CXCR4 mRNA; according to another aspect of the present invention the target mRNA may be an SDF-1 mRNA.

In addition to antisense oligonucleotides, another inhibitory nucleic acid may comprise an RNAi component. RNAi is inhibitory RNA. Restriction of foreign nucleic acids such as viruses and transposable elements (transposons) by RNAi mechanisms is an inherent and naturally occurring phenomenon in many plants, vertebrates and invertebrates, and constitutes an "immune system" at the genetic level. RNAi is a phenomenon in which a double stranded RNA (dsRNA) that is related in sequence to a specific mRNA can cause a selective degradation of that RNA.

One aspect of the RNAi mechanism involves a double stranded RNA (dsRNA) molecule which is cleaved within the cell by an enzyme termed "Dicer", resulting in fragments of the original dsRNA comprising about 21 to about 23 nucleotides in length, or consisting of a double stranded RNA fragment 21 to 23 nucleotides in length. These short interfering RNA fragments (siRNA) have a 5' phosphate and 3' hydroxyl and a 3' overhang normally comprising 2-3 nucleotides at each end. In other aspects of the invention the siRNA is designed and used without a dsRNA precursor. Certain aspects may have longer overhangs, including 3 or 4 nucleotides.

The siRNA then associates with a protein complex called the RNA induced silencing complex (RISC). This complex comprises a multiple components, and is activated by ATP. The activities associated with the complex include a helicase, a dsRNA nuclease and an RNA-dependent RNA polymerase activity; all these activities have been found to be essential for RNAi in *Drosophila, C. elegans*, and *Neurospora*. The siRNA permits the complex to be targeted to a particular mRNA. Once the RISC has bound to the target mRNA, there is an ATP-independent cleavage of the target RNA by an RISC-associated RNAse activity termed Slicer.

Relatively few dsRNA molecules are required to induced gene silencing. Thus, there appears to be a catalytic or amplification mechanism at work. The RNA-dependent RNAse activity appears to produce secondary siRNAs through an amplification process in which the original siRNA is primer extended using the target mRNA as a template in a manner similar to PCR.

The delivery of either long (dsRNA) or short (siRNA) RNA species to cells results in a certain amount of toxicity through the induction of the stress-response pathway (also called the interferon response) in vertebrates; however seems siRNA is slower to induce toxicity and the degree of such toxicity is generally less severe than dsRNA. Additionally, most of the studies that show toxicity of the dsRNA employed cationic lipids as a deliver device. Other deliver methods, such as those involving intracellular dsRNA synthesis using expression vectors, appear to induce gene silencing without induction of the stress response.

Introduction of nucleic acids within targeted cells has traditionally involved lipofection, electroporation, and microinjection. More recently, vector based RNAi expression systems such as those disclosed in Lee et al., 19 Nature Biotechnology 500 (May, 2002); Miyagishi et al., 19 Nature Biotechnology 497 (May 2002) and Tuschl, 20 Nature Biotechnology 446 (May 2002) have been demonstrated as capable of producing siRNA for downregulating gene expression in mammalian cells. These references are hereby incorporated herein by reference in their entirety.

As a means for silencing either or both CXCR4 and SDF-1 gene expression, RNAi may be quite useful as a therapeutic agent (an inhibitor of CXCR4 activity). RNAi may, without limitation, be administered by injection as naked dRNA or siRNA or in a liposome, implant, expression vector, viral vector, and the like (or a combination of one or more of these methods) directed into the in vitreous of the eye. As the drug is not given systemically, there would be less toxicity expected than for systemically administered drugs. Also, the catalytic or amplified nature of the gene-silencing phenomenon described above make RNAi a very attractive therapeutic method generally. For example, relatively few dsRNA and/or siRNA molecules might be required to induce a gene-silencing phenomenon in any tissue to which the RNA is applied.

Exemplary Conditions Treatable Through Inhibition of CXCR4 and or SDF-1

The inhibitors of CXCR4 activity have a desired ocular therapeutic effect. A desired ocular therapeutic effect includes the ability to prevent or reduce the extent of ocular cell death; for example, without limitation, neural cell death or RPE cell death by, for example, necrosis or apoptosis. Additionally, the therapeutic compounds of the present invention may be used to prevent or lessen the extent or rate of neovascularization in the posterior segment of the eye. Further, the therapeutic compounds of the present invention may be used to treat conditions, particularly, though not exclusively, retinal conditions, implicating acute or chronic inflammation in the eye.

Such conditions may include, without limitation, acute macular neuroretinopathy; Behcet's disease; choroidal neovascularization; diabetic uveitis; macular degeneration, such as acute macular degeneration, non-exudative age related macular degeneration and exudative age related macular degeneration; edema, such as macular edema, cystoid macular edema and diabetic macular edema; multifocal choroiditis; ocular tumors; retinal disorders, such as central retinal vein occlusion, diabetic retinopathy (including proliferative diabetic retinopathy), proliferative vitreoretinopathy (PVR), retinal arterial occlusive disease, uveitic retinal disease; branch retinal vein occlusion. These and other conditions may be grouped together as follows:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome.

PROLIFERATIVE DISORDERS: Proliferative Vitreal Retinopathy and Epiretinal Membranes, Proliferative Diabetic Retinopathy, Retinopathy of Prematurity (retrolental fibroplastic).

TUMORS: Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis, Ocular inflammatory and immune disorders, ocular vascular malfunctions, Corneal Graft Rejection, Neovascular Glaucoma and the like.

The therapeutic compounds of, and used in, the present invention can be administered in any way suitable to effectively achieve a desired ocular therapeutic effect. Thus, methods of administration may include without limitation, topical, intraocular (including intravitreal), transdermal, oral, intravenous, subconjunctival, subretinal, or peritoneal.

Generally, topical and intraocular (e.g., intravitreal, subconjunctival and subretinal) methods of administration of the CXCR4 inhibitors of the present invention may often be preferred; as such means of administration avoid many of the possible disadvantages of systemic administration, such as undesired side effects in tissues other than the eye. Without Of these, and without regard to the particular chemistry involved with each agent or agent class, topical administration may generally be initially preferable from the point of view of ease of use, a comparably low degree of ocular trauma, and relatively few risks associated with the means of administration itself.

However, agents that are applied topically to the ocular surface topically may have a very short residence time on the cornea. Generally, and depending in part on factors such as hydrophilicity, blood supply, specific activity, and nature of the drug (such as size, stability and shape), topical drug delivery can deliver therapeutic concentrations of the drug to anterior segment features such as the cornea, anterior chamber, iris, lens and cilary body of the eye, but drug delivery to posterior segment features such as the vitreous humor, retinal pigmented epithelium, retina and choroid is less effective. Theoretically, drug applied topically to the eye can diffuse through the conjunctiva and sclera, and then penetrate the eye through the iris route or the retinal pigmented epithelium (RPE). However, this creates a very large diffusional path length and the tissues pose a considerable barrier, with the choroid blood-flow and the resistance of the conjunctiva and the RPE. In practice, topically applied ophthalmic drugs often do not achieve therapeutic concentrations in the posterior segment tissues. Additionally, topically applied macromolecular CXCR4 inhibitors may, in many cases, be too large to quickly diffuse into the tissue of the posterior segment.

Formulation Vehicles

Regardless of the mode of administration or form (e.g., without limitation, in solution, suspension, cream, gel, as a topical, injectable or implantable agent), the therapeutic compositions of the present invention will be administered in a pharmaceutically acceptable vehicle component. The therapeutic agent (or agents) may also be combined with a pharmaceutically acceptable vehicle component in the manufacture of a composition. In other words, a composition, as disclosed herein, may comprise a CXCR4 inhibitor and an effective amount of a pharmaceutically acceptable vehicle component. In at least one embodiment, the vehicle component is aqueous-based. For example, the composition may comprise water.

In certain embodiments such as in placement into the vitreous, or under the conjunctiva or retina, the CXCR4 inhibitor is administered in a vehicle component, and may also include an effective amount of at least one of a viscosity inducing component, a resuspension component, a preservative component, a tonicity component and a buffer component. In some embodiments, the compositions disclosed herein include no added preservative component. In other embodiments, a composition may optionally include an added preservative component. In addition, the composition may be included with no resuspension component.

Presently, subconjunctival delivery is a very attractive possibility, as retinal diffusion appears to be greater than seen with topical delivery, and the administration of the drug is not as traumatic as intraocular delivery (such as intravitreal and sub retinal placement or injection). Subconjunctival delivery may include injection of a solution or suspension containing the CXCR4 inhibitor, and/or the administration of an implant, such as a biodegradable matrix comprising, for example, a poly lactoside poly glycoside co-polymer designed to release the active drug over a pre-determined period of time.

However, this is not to say that intravitreal and subretinal administration means may not be effectively used too. Indeed, intraocular means are the most direct way of contacting the affected retinal tissue with the therapeutic agent. In such cases, as with subconjunctival delivery, liquid solutions or suspensions, usually having a viscosity and a refractive index greater than that of water (to prevent adversely affecting the viscosity of the vitreous humor and thus the vision of the patient).

Additional delivery means may include injection to the muscular tissues of the orbit or to the upper or lower eyelid. While these means may indeed be effective in delivering the CXCR4 inhibitors of the present invention (particularly in the case of small and/or lipophilic compounds), these means are not now currently preferred.

In preferred embodiments of the present invention formulations Formulations for topical, subconjunctival, subretinal or intraocular administration of the therapeutic agents (including, without limitation, implants or particles containing such agents) will preferably include a major amount of liquid water. Such compositions are preferably formulated in a sterile form, for example, prior to being used in the eye. The above-mentioned buffer component, if present in the formulations, is present in an amount effective to control the pH of the composition. The formulations may contain, either in addition to, or instead of the buffer component at least one tonicity component in an amount effective to control the tonicity or osmolality of the compositions. Indeed, the same component may serve as both a buffer component and a tonicity component. More preferably, the present compositions may include both a buffer component and a tonicity component.

The buffer component and/or tonicity component, if either is present, may be chosen from those that are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof. Non-ionic tonicity components may comprise polyols derived from sugars, such as xylitol, sorbitol, mannitol, glycerol and the like.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The compositions of, or used in, the present invention may include one or more other components in amounts effective to provide one or more useful properties and/or benefits to the present compositions. For example, although the present compositions may be substantially free of added preservative components, in other embodiments, the present compositions include effective amounts of preservative components, preferably such components that are more compatible with or friendly to the tissue in the posterior segment of the eye into which the composition is placed than benzyl alcohol. Examples of such preservative components include, without limitation, quaternary ammonium preservatives such as benzalkonium chloride ("BAC" or "BAK") and polyoxamer; biguanidebigunanide preservatives such as polyhexamethylene biguanidebiguandide (PHMB); methyl and ethyl parabens; hexetidine; chlorite components, such as stabilized chlorine dioxide, metal chlorites and the like; other ophthalmically acceptable preservatives and the like and mixtures thereof. The concentration of the preservative component, if any, in the present compositions is a concentration effective to preserve the composition, and (depending on the nature of the particular preservative used) is often and generally used in a range of about 0.00001% to about 0.05% (w/v) or about 0.1% (w/v) of the composition.

Intravitreal delivery of therapeutic agents can be achieved by injecting a liquid-containing composition into the vitreous, or by placing polymeric drug delivery systems, such as implants and microparticles comprising the therapeutic agent, such as microspheres, or a rod, wafer of other shaped implant, into the vitreous. Examples of biocompatible implants for placement in the eye have been disclosed in a number of patents, such as U.S. Pat. Nos. 4,521,210; 4,853,224; 4,997,652; 5,164,188; 5,443,505; 5,501,856; 5,632,984; 5,766,242; 5,824,072; 5,869,079; 6,074,661; 6,331,313; 6,369,116; 6,699,493; 6,726,918, hereby incorporated by reference herein.

Similar methods may be used for subconjunctival or subretinal delivery of the drug. If an implant is used, the implant may be placed (e.g., injected) under the conjunctiva at a location proximal to the back of the eye. A suspension or liquid based formulation would be administered so as to remain under the conjunctival membrane, effectively using it as a depot for sustained release of the CXCR4 inhibitor. In either case, release of the CXCR4 inhibitor will occur over a period of time and will not have to travel as far around the circumference of the scleraschlera or through the anterior segment as topically applied drug would need to travel. An advantage to this mode of delivery, is that no puncture of the eye itself is required.

Subretinal placement of an implant involves some trauma to the eye, but does nor require puncture of the eyeball, as does intravitreal injection. The risk of severe consequences of infection is not as great when the vitreous is not punctured.

Formulations containing the therapeutic agents of the present invention can be produced using conventional techniques routinely known by persons of ordinary skill in the art. For example, a CXCR4 inhibitor can be combined with a liquid carrier. The composition can be sterilized or sterile components mixed. In certain embodiments, such as preservative-free embodiments, the compositions can be sterilized and packaged in single-dose amounts. The compositions may be prepackaged in dispensers that can be disposed of after a single administration of the unit dose of the compositions.

The compositions comprising the inhibitors of CXCR4 activity can be prepared using suitable blending/processing techniques, for example, one or more conventional blending techniques. The preparation processing should be chosen to provide such inhibitors in implants having as form useful for intravitreal, subconjunctival, subretinal or periocular placement or injection into eyes of humans or animals.

For example, in one useful embodiment a concentrated therapeutic component dispersion is made by combining the therapeutic component with water, and the excipients (other than a viscosity inducing component) to be included in the final composition. The ingredients are mixed to disperse the therapeutic component and then autoclaved. Viscosity inducing component may be purchased sterile or sterilized by conventional processing, for example, by filtering a dilute solution followed by lyophylization to yield a sterile powder. The sterile viscosity-inducing component is combined with water to make an aqueous concentrate. The concentrated therapeutic component dispersion is mixed and added as a slurry to the viscosity inducing component concentrate. Water is added in a quantity sufficient (q.s.) to provide the desired composition and the composition is mixed until homogenous.

In one embodiment, a sterile, viscous suspension suitable for administration is made using an inhibitor of CXCR4 activity. A process for producing such a composition may comprise sterile suspension bulk compounding and aseptic filling.

Other embodiments of the present materials are in the form of a polymeric drug delivery system that is capable of providing sustained drug delivery for extended periods of time after a single administration. For example, the present drug delivery systems can release the inhibitor of CXCR4 activity for at least about two weeks, or about three weeks, or 1 month, or about 3 months, or about 6 months, or about 1 year, or about 5 years or more. Thus, such embodiments of the present materials may comprise a polymeric component associated with the therapeutic component in the form of a polymeric drug delivery system suitable for administration to a patient by at least one of intravitreal, subconjunctival, subretinal and periocular administration.

The polymeric drug delivery system may be in the form of biodegradable polymeric implants, non-biodegradable polymeric implants, biodegradable polymeric microparticles, and combinations thereof. Implants may be in the form of rods, wafers, sheets, filaments, spheres, and the like. Particles are generally smaller than the implants disclosed herein, and may vary in shape. For example, certain embodiments of the present invention utilize substantially spherical particles. These particles may be in the form of microspheres. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurement.

As discussed herein, the polymeric component of the implantable drug delivery systems can comprise a polymer selected from the group consisting of biodegradable polymers, non-biodegradable polymers, biodegradable copolymers, non-biodegradable copolymers, and combinations thereof. In certain embodiments, the polymeric component comprises a poly (lactide-co-glycolide) polymer (PLGA). In other embodiments, the polymeric component comprises a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof. The polymeric component may be associated with the therapeutic component to form an implant selected from the group consisting of solid implants, semisolid implants, and viscoelastic implants.

In additional embodiments, the polymeric component may comprise any polymeric material useful in a body of a mammal, whether derived from a natural source or synthetic. Some additional examples of useful polymeric materials for the purposes of this invention include carbohydrate based polymers such as methylcellulose, carboxymethylcellulose, hydroxymethylcellulose hydroxypropylcellulose, hydroxyethylcellulose, ethyl cellulose, dextrin, cyclodextrins, alginate, hyaluronic acid and chitosan, protein based polymers such as gelatin, collagen and glycolproteins, and hydroxy acid polyesters such as polyglycolide, polyhydroxybutyric acid, polycaprolactone, polyvalerolactone, polyphosphazene, and polyorthoesters. Polymers can also be crosslinked, blended or used as copolymers in the implant. Other polymer carriers include albumin, polyanhydrides, polyethylene glycols, polyvinyl polyhydroxyalkyl methacrylates, pyrrolidone and polyvinyl alcohol.

Some examples of non-erodible polymers include silicone, polycarbonates, polyvinyl chlorides, polyamides, polysulfones, polyvinyl acetates, polyurethane, ethylvinyl acetate derivatives, acrylic resins, crosslinked polyvinyl alcohol and crosslinked polyvinylpyrrolidone, polystyrene and cellulose acetate derivatives.

These additional polymeric materials may be useful with any of the CXCR4 inhibitors disclosed herein. For example, and without limitation, particles of PLA or PLGA may be coupled to a CXCR4 inhibitor. This insoluble tripartite conjugate will slowly erode over time, thereby continuously releasing the CXCR4 inhibitor.

The inhibitor of CXCR4 activity may be wholly or partly in a particulate or powder form and entrapped by a biodegradable polymer matrix. If in a particulate form (for example, a crystalline or microcrystalline form), particles in intraocular, subconjunctival, or subretinal implants will generally have an effective average size measuring less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric component, the resulting polymeric particles may be used to provide a desired therapeutic effect.

If formulated as part of an implant or other drug delivery system, (and particularly if not in the form of an expression vector) the inhibitor of CXCR4 activity may be preferably from about 1% to 90% by weight of the drug delivery system. More preferably, such an inhibitor of CXCR4 activity is from about 20% to about 80% by weight of the system. In a preferred embodiment, the CXCR4 inhibitor GD comprises about 40% by weight of the system (e.g., 30%-50%). In another embodiment, the CXCR4 inhibitor GD comprises about 60% by weight of the system.

Suitable polymeric materials or compositions for use in the drug delivery systems include those materials that are compatible, e.g., biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, *Biodegradable Polymers in Controlled Drug Delivery*, In: CRC CRITICAL REVIEWS IN THERAPEUTIC DRUG CARRIER SYSTEMS, VOL. 1, CRC Press, Boca Raton, Fla. 1987, pp 39-90, incorporated by reference herein, which describes encapsulation for controlled drug delivery, may find use in the present drug delivery systems.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present systems may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Also important to controlling the biodegradation of the polymer and hence the extended release profile of the drug delivery systems is the relative average molecular weight of the polymeric composition employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix may comprise a mixture of two or more biodegradable polymers. For example, the system may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component in this aspect of the present invention is associated with the CXCR4 inhibitor so that the release of the therapeutic component into the eye is by one or more of diffusion, erosion, dissolution, and osmosis. As discussed herein, the matrix of an intraocular, subconjunctival, periocular or subretinal drug delivery system may release drug at a rate effective to sustain release of an amount of the therapeutic agent for more than one week after implantation into an eye. In certain systems, therapeutic amounts of the CXCR4 inhibitor are released for more than about one month, and even for about twelve months or more. For example, the therapeutic component can be released into the eye for a time period from about ninety days to about one year after the system is placed in the interior of an eye.

The release of the CXCR4 inhibitor from the drug delivery systems comprising a biodegradable polymer matrix may include an initial burst of release (for example, about 20%, or about 30%, or about 40%, or about 50%, or about 60%, or about 70%, or about 80% of the CXCR4 inhibitor is released in the first 3 day after implantation), followed by a gradual increase in the amount of the inhibitor released, or the release may include an initial delay in release of the CXCR4 inhibitor followed by an increase in release. When the system is substantially completely degraded, the percent of the therapeutic agent that has been released is about one hundred.

It may be desirable to provide a relatively constant rate of release of the therapeutic agent from the drug delivery system over the life of the system. For example, it may be desirable for the CXCR4 inhibitor to be released in amounts from about 0.01 μg to about 2 μg per day for the life of the system. However, the release rate may change to either increase or decrease depending on the formulation of the biodegradable polymer matrix. In addition, the release profile of the CXCR4 inhibitor may include one or more linear portions and/or one or more non-linear portions. Preferably, the release rate is greater than zero once the system has begun to degrade or erode.

The drug delivery systems, such as the intraocular implants, may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the CXCR4 inhibitor falls within a narrow window. In addition, the therapeutic component, including the therapeutic agent(s) described herein, may be distributed in a non-homogenous pattern in the matrix. For example, the drug delivery system may include a portion that has a greater concentration of the CXCR4 inhibitor relative to a second portion of the system.

The polymeric implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by implantation. The vitreous chamber (and the subconjunctiva) in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, under the conjunctiva, or under the retina, and accommodation of the implant. The total weight of the implant is usually about 250-5000 μg, more preferably about 500-1000 μg. For example, an implant may be about 500 μg, or about 1000 μg. However, larger implants may also be formed and further processed before administration to an eye. In addition, larger implants may be desirable where relatively greater amounts of the CXCR4 inhibitor are provided in the implant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of the CXCR4 inhibitor, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems may be of any geometry suitable to the delivery means including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the system can also be used to control the rate of release.

Other route of administering the CXCR4 inhibitors of the present invention to the interior of the eye may include periocular delivery of drugs to a patient. The blood-retinal barriers often restrict penetration of systemically administered drugs directly into the posterior segment of the eye. The blood-retinal barrier is anatomically separated into inner and outer blood barriers. Movement of solutes or drugs into the interior of the eye from the periocular space is restricted by the retinal pigment epithelium (RPE), the outer blood-retinal barrier. Intercellular junctions termed zona occludens or "tight junctions" join the cells of this tissue. The RPE is a tight ion-transporting barrier that restricts paracellular transport of solutes across the RPE. The permeability of most compounds across the blood-retinal barriers is very low. However, the RPE itself possesses the singular ability to quickly take up extracellular agents by phagocytosis, thus this fact vitiates in favor of extrasystemic transport to the retina.

Formulations Containing CXCR4 Inhibitors

The CXCR4 inhibitors (including vectors, oligonucleotides and polypeptides and/or conjugates thereof) of the present invention may be suspended in a viscous formulation having a relatively high viscosity, such as one approximating that of the vitreous humor. Such viscous formulation comprises a viscosity-inducing component. In addition to the use of implants, the CXCR4 inhibitors of the present invention may be administered subconjunctivally, subretinally, or intravitreally as, without limitation, an aqueous injection, a suspension, an emulsion, a solution, a gel.

The viscosity-inducing component preferably comprises a polymeric component and/or at least one viscoelastic agent, such as those materials that are useful in ophthalmic surgical procedures.

Examples of useful viscosity inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the presently useful viscosity inducing components may be in a range up to about 2 million Daltons, such as of about 10,000 Daltons or less to about 2 million Daltons or more. In one particularly useful embodiment, the molecular weight of the viscosity-inducing component is in a range of about 100,000 Daltons or about 200,000 Daltons to about 1 million Daltons or about 1.5 million Daltons.

In one very useful embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons.

In one embodiment, the present compositions are comprised in, or comprise, a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows the sedimentation rate of any suspended drug, and prevents pooling of injected drug product.

The CXCR4 inhibitors of this aspect of the claimed invention may, depending on their physiochemical characteristics, include any or all salts, prodrugs, conjugates, or precursors of therapeutically useful agents, including those specifically identified herein.

In certain embodiments, the CXCR4 inhibitors of the composition may be comprised in a composition comprising more than one therapeutic agent, so long as at least one such therapeutic agent is able to inhibit CXCR4 activity. In other words, the therapeutic component of the composition may include a first CXCR4 inhibitor, a second CXCR4 inhibitor, or a combination of therapeutic agents at least one of which is a CXCR4 inhibitor.

The viscosity-inducing component is present in an effective amount in increasing, advantageously substantially increasing, and the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the present compositions into the posterior segment, the relatively high viscosity of the present compositions are believed to enhance the ability of the present compositions of the present invention.

Advantageously, the compositions of this aspect of the invention have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. In particular embodiments the present compositions not only have the relatively high viscosity noted above but also have the ability or are structured or made up so as to be effectively able to be placed, e.g., injected, into a posterior segment of an eye of a human or animal, preferably through a 27 gauge needle, or even through a 30 gauge needle.

The viscosity inducing components preferably are shear thinning components such that as the viscous formulation is passed through or injected into the posterior segment of an eye, for example, through a narrow aperture, such as 27 gauge needle, under high shear conditions the viscosity of the composition is substantially reduced during such passage.

Any ophthalmically acceptable viscosity-inducing component may be employed in accordance with the present invention. Many such viscosity-inducing components have been proposed and/or used in ophthalmic compositions used on or in the eye. The viscosity-inducing component is present in an amount effective in providing the desired viscosity to the composition. Advantageously, the viscosity-inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and similar factors.

In another embodiment of the invention, the CXCR4 inhibitor may be delivered intraocularly or subconjunctivally in a composition that comprises, consists essentially of, or consists of, a therapeutic agent comprising a bioactive agent (the CXCR4 inhibitor), a transporter substrate, and a biocompatible polymer suitable for administration to the posterior segment of an eye. For example, the composition may, without limitation, comprise a subconjunctival, subretinal, or intraocular implant.

The present invention is generally drawn to methods for treating the posterior segment of the eye. Preferably, the posterior segment of the eye comprises, without limitation, the uveal tract, vitreous, retina, choroid, optic nerve, and the retinal pigmented epithelium (RPE). The disease or condition related to this invention may comprise any disease or condition associated with cell death, inflammation, or angiogenesis which is potentiated by the stimulation of the CXCR4 receptor.

While not intending to limit the scope of this invention in any way, some examples of diseases or conditions that can be prevented or treated by the action of an active drug upon the posterior part of the eye in accordance with the present invention include maculopathies/retinal degeneration such as macular edema, non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, inflammation of the retina, intermediate uveitis (pars planitis), multifocal choroiditis, subretinal fibrosis and uveitis syndrome, vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial micro aneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis. Preferably, the disease or condition is proliferative vitreal retinopathy (PVR), age-related macular degeneration (ARMD), diabetic retinopathy, diabetic macular edema, retinal detachment, macular edema, or uveitus.

The following examples illustrate examples of the present invention, and do not limit it in any way. The invention is defined solely by the claims that conclude this specification.

EXAMPLES

Example 1

Transfection of Cells with RNAi

ARPE 19 cells (American Type Tissue Collection (ATTC) Number CRL2302) were plated at a cell density of $6\times10^4$ cells per 10 cm tissue culture dish, in Delbecco's Modified Eagle's Medium (DMEM) F12 containing 10% fetal bovine serum (FBS) and 1% antibiotic/antimycotic solution (10,000 units of penicillin G (sodium salt), 10,000 μg/ml of streptomycin sulfate, and 25 μg/ml of amphotericin B in 0.85% saline) incubated at 37° C. overnight.

The anti-CXCR4 RNAi oligonucleotides, designed to make a double-stranded siRNA, comprise the following sequences:

```
5' AACAGUGGAAGAAAGCUAGGGGCUC 3'   (SEQ ID NO: 10)

5' GAGGCCCUAGCUUUCUUCCACUGUU 3'   (SEQ ID NO: 11)
```

These oligonucleotides or control oligonucleotides (Stealth RNAi negative control Med GC (Invitrogen, Inc.)) were added in 1.5 ml of OptiMem® media (Gibco BRL) to a final concentration of 25 nM. In a separate equal volume of OptiMem® media, 15 μl of lipofectamine reagent (Lipofectamine® 2000, Invitrogen, Inc.) was similarly added to equal volume of OptiMem® media and incubated at room temperature for 5 minutes.

Both solutions were then mixed together and further incubated for 20 minutes at room temperature. The cells were washed once with OptiMem® media, the total volume of the mixture was brought up to 10 ml with OptiMem® media (Gibco BRL) and then added to the cells. Cells were permitted to incubate overnight at 37° C. 24 hours following transfection, the transfection mixture was removed and 10 ml of fresh DMEM F12 media added to the cells.

Example 2

Oxidative Stress/Cell Viability Assay

Following transfection of the cells with the siRNA construct of SEQ ID NO: 10 and 11 (FIG. 1), or SEQ ID NO: 10-15 (FIG. 3), ARPE-19 cells were maintained in DMEM F12 medium containing 10% FBS, and 1% antibiotic/antimycotic solution (10,000 units of penicillin G (sodium salt), 10,000 μg/ml of streptomycin sulfate, and 25 μg/ml of amphotericin B in 0.85% saline) for 48 hrs. The cells were plated at a density of $1\times10^4$ cells per 100 μl well in a 96 well plate and incubated overnight at 37° C. and 5% CO2. The next day the cells were washed twice with DMEM F12 containing 0.1% FBS and 1% antibiotic/antimycotic solution (10,000 units of penicillin G (sodium salt), 10,000 μg/ml of streptomycin sulfate, and 25 μg/ml of amphotericin B in 0.85% saline).

After washing, the cells were starved for 24 hours in the same media, at 37° C. for 24 hours. Following this period of time, the cells were exposed to tertiary-butylhydroperoxide (t-BH) at a final concentration of 300 μM for 6 hours. The cells were then washed twice with DMEM F12 medium containing 0.1% FBS and 1% antibiotic/antimycotic solution (10,000 units of penicillin G (sodium salt), 10,000 μg/ml of streptomycin sulfate, and 25 μg/ml of amphotericin B in 0.85% saline). Fresh media was added and the cells incubated further in a volume of 100 μl at 37° C. for a total of 24 hours from the initiation of t-BH treatment.

Cell viability was measured using the WST assay (Chemicon International, Inc.) according to the manufacturer's instructions. The WST assay is based on the cleavage of the tetrazolium salt WST-1 to formazan by cellular mitochondrial dehydrogenases. Expansion in the number of viable cells results in an increase in the overall activity of the mitochondrial dehydrogenases in the sample. An increase in enzyme activity due to greater numbers of cells leads to an increase in the amount of formazan dye formed. Thus, the formazan dye produced by viable cells can be quantified by a multiwell spectrophotometer (microplate reader) by measuring the absorbance of the dye solution at 440 nm.

In this case, 10 μl of WST-1 reagent was added to each well after 24 hours. The optimum assay development time was determined to be 1.5 hours. Plates were then read in a Spectramax M2 Platereader® at 450 nm.

To isolate RNA from cells, 1 ml Qiazol® (a phenol/guanidinium isothiocyanate-based RNAse inhibitory lysis buffer sold by Qiagen, Inc.) was added to the ARPE-19 cells and the lysates then scraped into 2 ml tubes. 200 μl of chloroform per ml of Qiazol® was then added, the tubes mixed and centrifuged at 12,000×g for 15 minutes at 4° C. The aqueous phase was removed and applied to an RNeasy® mini column (Qiagen), washed and the column eluted with water. Five micrograms of the eluate were used for subsequent RT-PCR reactions. RT-PCR reactions were carried out using the Stratascript® First Strand Synthesis System (Stratagene). The RNA was denatured at 65° C. for 5 minutes, cooled at RT for 10 minutes then incubated at 42° C. for 60 minutes with reverse transcriptase.

Quantitative PCR was conducted using 5 ul of cDNA generated by RT-PCR. Platinum qPCR Supermix®-UDG assay (Invitrogen) was used for the amplification. The PCR reaction was carried out for 45 cycles using the following conditions: 50° C. for 2 minutes, 95° C. for 2 minutes, 95° C. for 15 seconds, 60° C. for 45 seconds. GAPDH was used to normalize expression levels. Reactions and analysis were carried out using an ABI Prism 7700 Sequence Detector.

Example 3

Whole Genome Array

A whole human genome DNA oligonucleotide array (Agilent Technnologies, G4112A array) was used to hybridize against RNA samples prepared from ARPE-19 cells treated with t-BH. This 44K slide format contains a collection of 60-mer oligonucleotides with sequences representing over 41 K human genes and transcripts.

RNA labeling was performed using the Low RNA Input Fluorescent Linear Amplification kit (LIK®) from Agilent Technologies (#5184-3523) following the manufacturer's recommendations. Briefly, 200 ng of total RNA from the ARPE-19 cells isolated as described in Example 2 were reverse transcribed in a 20 μL volume using with 1 μL Moloney Murine Leukemia Virus reverse transcriptase (MMLV-RT) and 1.2 μL of T7 promoter primer in 1× First Strand Buffer at 40° C. for 2 hours. From the double-stranded DNA preparation, transcription and direct labeling were prepared in 80 μL at 40° C. for 2 hours using 0.8 μL of T7 RNA polymerase, 0.6 μL inorganic pyrrophosphatase, 2.4 μL of each Cy-dye-CTP at 10 mM (PerkinElmer/NEN Life Sciences Cyanine-3-CTP #NEL580 and Cyanine-5-CTP #NEL581) in 4% PEG solution and 1× Transcription buffer. Cyanine dyes are highly sensitive fluorescent dyes.

Amplified and labeled cRNA was purified on Rneasy® mini columns (Qiagen, Inc.) according to manufacturer's protocol. cRNA was quantified by absorbance at 260 nm, 550 nm and 650 nm. Once labeling is complete, both Cy3 and Cy5 RNA samples are combined and hybridized to the microarray using the Agilent In Situ Hybridization kit (#5184-3568) following Agilent's recommendations.

Briefly 750 ng of cyanine 3-labeled linearly amplified cRNA and 750 ng of cyanine 5-labeled linearly amplified cRNA are combined to 1× control targets, 0.5× fragmentation buffer. This 2× target solution is denaturated at 60° C. for 30 minutes and 1× hybridization buffer in a 500 μL final volume is added to terminate the fragmentation reaction.

The target solution is then dispensed onto the 44K microarray. Incubation time was 17 hours at 60° C. in a hybridization oven with rotation at 4 rpm (Agilent Technologies #G2545A). Washes were performed for 5 minutes in 6×SSPE, 0.005% N-lauroyl sarcosine at room temperature, then for 5 minutes in 0.06×SSPE, 0.005% N-lauroyl sarcosine at room temperature, and finally for 30 seconds in Agilent Stabilization and Drying Solution®. The dried slides were scanned using a microarray scanner.

FIG. 1 demonstrates the expression of CXCR4 mRNA in ARPE4-19 cells in oxidative stress model (exposure to t-BH for 30 minutes, 3 hours, and 6 hours. RNA was harvested immediately following t-BH exposure, except aliquots of cells exposed to t-BH for 3 hours were also incubated for a total of three additional hours (3/3) or 24 hours (3/24) after their exposure to t-BH, then RNA was harvested. Whole human genome arrays were permitted to hybridize the isolated RNA, using untreated cells as a baseline.

The results indicate that the expression of CXCR4 RNA increases quickly in cells exposed to stress, with a 20-fold increase in such expression immediately after three hours' exposure to t-BH, and 30-fold expression over baseline immediately after six hours' incubation with t-BH. There is almost no reduction in CXCR4 expression in cells exposed to t-BH for three hours upon a further three hours' incubation in t-BH-free medium, but an approximately 35% decrease in CXCR4 RNA can be seen in cells exposed to t-BH for three hours upon a further twenty four hours' incubation in t-BH-free medium, as compared to the levels present immediately following exposure to t-BH.

Additionally, cells exposed to t-BH for 6 hours resulted in cell death by 24 hours. However, among the cells exposed to t-BH for 3 hours, following by incubation of cells in non t-BH-containing media, approximately 70% survived for at least 24 hours.

Figure 2:
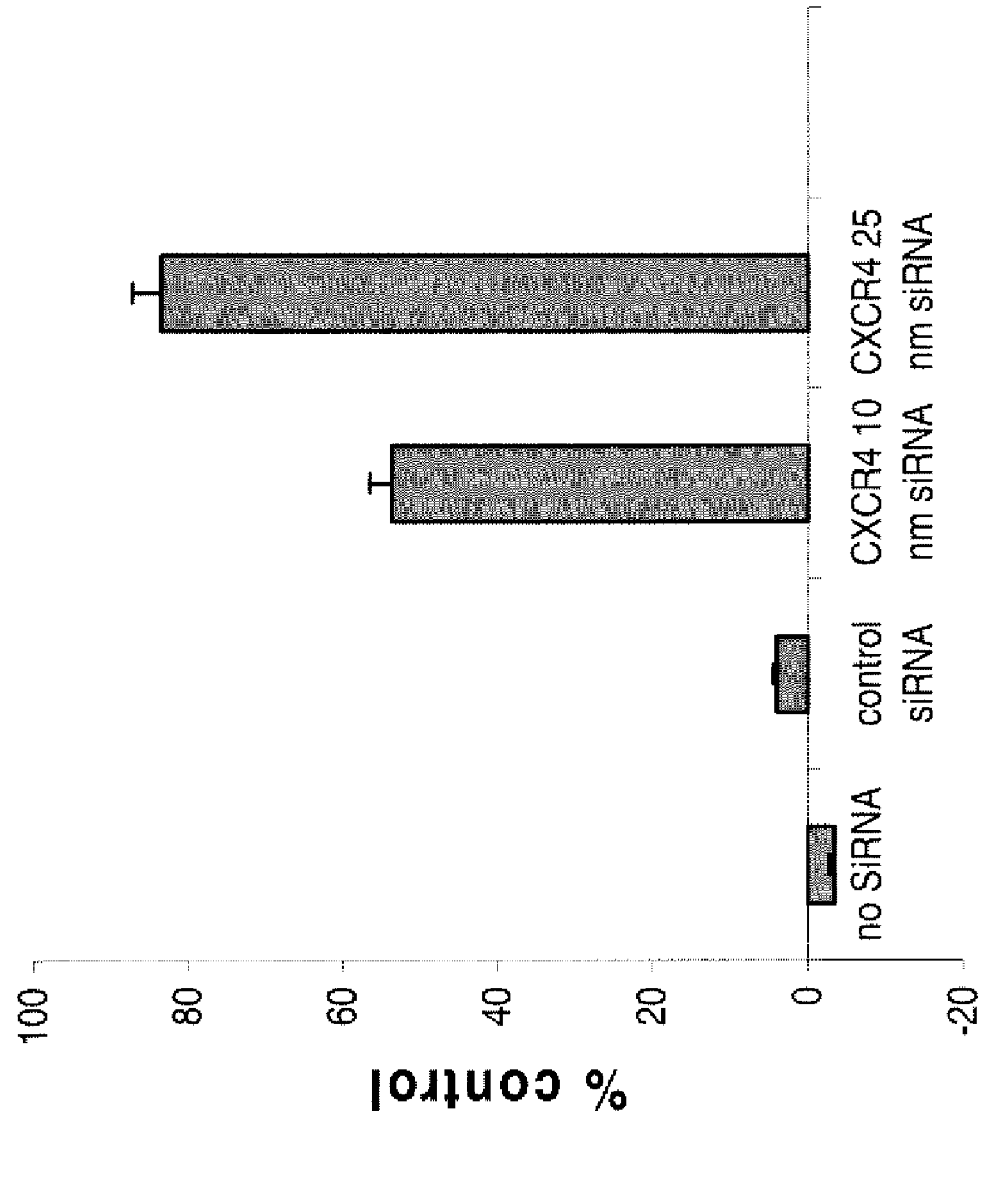
FIG. 2 shows that siRNA inhibition of CXCR4 expression in ARPE-19 cells inhibits the cell death induced by oxidative stress (exposure to 300 uM t-BH) in a dose-dependent fashion.

FIG. 2 shows that siRNA inhibition of CXCR4 expression in ARPE-19 cells inhibits the cell death induced by oxidative stress (exposure to 300 uM t-BH) in a dose-dependent fashion. A WST cell viability assay was performed using naive cells or cells exposed to t-BH for 6 hours and transfected either with control oligonucleotides or with siRNA oligonucleotides of SEQ ID NO: 10 and SEQ ID NO: 11 at 10 nM or 25 nM.

Figure 3:
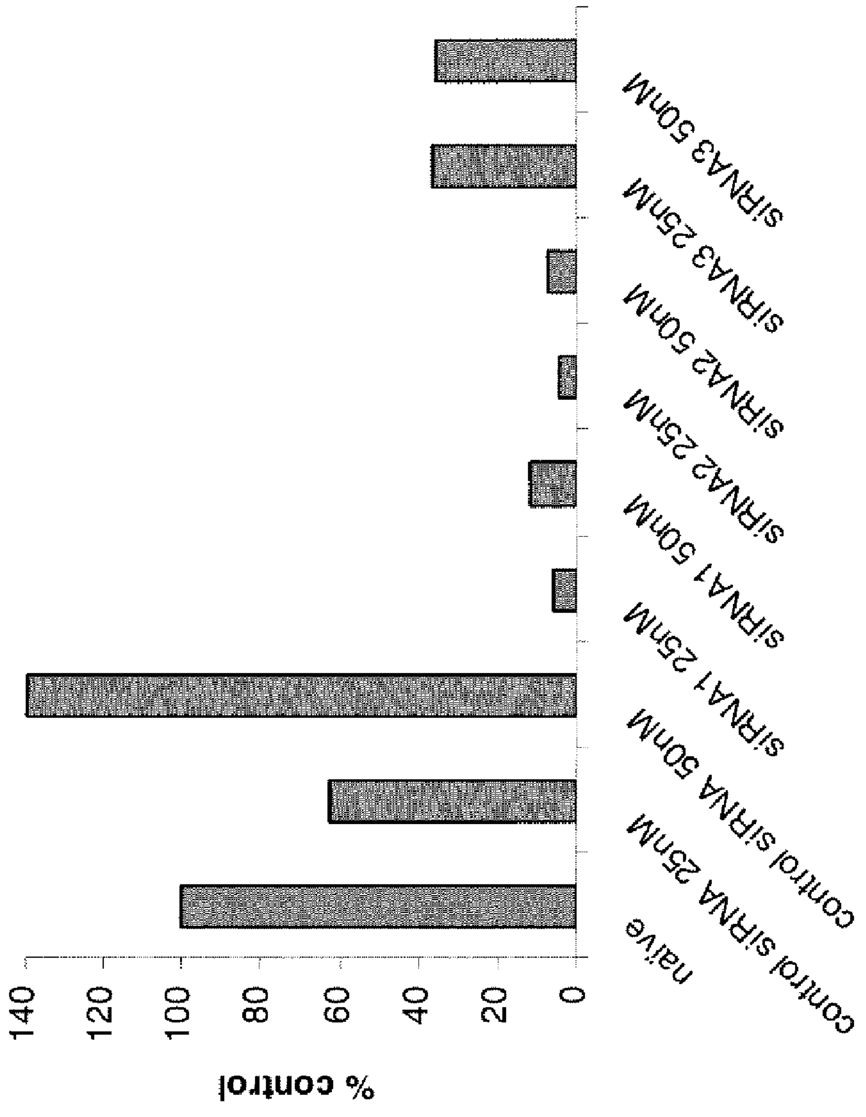
FIG. 3 shows the results of an experiment in which expression of cells transfected with siRNA Pair 1 (siRNA1; SEQ ID NO: 10, SEQ ID NO: 11), Pair 2 (siRNA2; SEQ ID NO: 12, SEQ ID NO: 13), and Pair 3 (siRNA3; SEQ ID NO: 14, SEQ ID NO: 15) was examined.

FIG. 3 shows the results of an experiment in which expression of cells transfected with siRNA Pair 1 (siRNA1; SEQ ID NO: 10, SEQ ID NO: 11), Pair 2 (siRNA2; SEQ ID NO: 12, SEQ ID NO: 13), and Pair 3 (siRNA3; SEQ ID NO: 14, SEQ ID NO: 15) was examined. Pair 2 and Pair 3 siRNA oligonucleotides are shown below:

Pair 2

```
5' aacaguggaagaaagcuagggccuc 3'   (SEQ ID NO: 12)

5' gaggcccuagcuuucuuccacuguu 3'   (SEQ ID NO: 13)
```

Pair 3

```
5' cuuggagugugacagcuuggagaug 3'   (SEQ ID NO: 14)

5' caucuccaagcugucacacuccaag 3'   (SEQ ID NO: 15)
```

Total RNA was isolated from the cells (uninduced with t-BH) and the amount of CXCR4 RNA determined by gene array hybridization. The amount of CXCR4 in the naïve cells are standardized as "100%". As shown, all the siRNA pairs tested (Pair 1, 2 and 3) reduce the expression of intact intracellular CXCR4 RNA as compared to both cells untreated with siRNA, or with cells given a "non-functional" control siRNA. These results, combined with those illustrated in FIG. 2 show that apoptosis decreased with decreasing CXCR4 expression, and that treatment of stressed, CXCR4 expressing cells with anti-CXCR4 siRNA restores cell viability to levels approaching normal.

Example 4

A similar set of experiments to those described in Examples 1-3 above are conducted using each of the following anti CXCR4 siRNAs:

Pair 4

```
5'-cccaccaucuacuccaucaucuucu      (SEQ ID NO: 36)

5'-agaagaugauggaguagaugguggg      (SEQ ID NO: 37)
```

Pair 5

```
5'-accaucuacuccaucaucuucuuaa      (SEQ ID NO: 38)

5'-uuaagaagaugauggaguagauggu      (SEQ ID NO: 39)
```

Pair 6

```
5'-caucaucuucuuaacuggcauugug      (SEQ ID NO: 40)

5'-cacaaugccaguuaagaagaugaug      (SEQ ID NO: 41)
```

Pair 7

```
5'-ggcaauggauuggucauccugguca      (SEQ ID NO: 42)

5'-ugaccaggaugaccaauccauugcc      (SEQ ID NO: 43)
```

Pair 8

```
5'-ugguuggccuuauccugccugguau      (SEQ ID NO: 44)

5'-auaccaggcaggauaaggccaacca      (SEQ ID NO: 45)
```

Pair 9

```
5'-ucuucgccuguuggcugccuuacua      (SEQ ID NO: 46)

5'-uaguaaggcagccaacaggcgaaga      (SEQ ID NO: 47)
```

Pair 10

5'-cgccuguuggcugccuuacuacauu (SEQ ID NO: 48)

5'-aauguaguaaggcagccaacaggcg (SEQ ID NO: 49)

Pair 11

5'-gaggcccuagcuuucuuccacuguu (SEQ ID NO: 50)

5'-aacaguggaagaaagcuagggccuc (SEQ ID NO: 51)

Pair 12

5'-caaaggaaagcgagguggacauuca (SEQ ID NO: 52)

5'-ugaauguccaccucgcuuuccuuug (SEQ ID NO: 53)

Pair 13

5'-aaagcgagguggacauucaucuguu (SEQ ID NO: 54)

5'-aacagaugaauguccaccucgcuuu (SEQ ID NO: 55)

Pair c

5'-acacuccaaacugugcccuucagau (SEQ ID NO: 20)

5'-aucugaagggcacaguuuggagugu (SEQ ID NO: 21)

Pair d

5'-caagugugcauugacccgaagcuaa (SEQ ID NO: 22)

5'-uuagcuucgggucaaugcacacuug (SEQ ID NO: 23)

Pair e

5'-aagugugcauugacccgaagcuaaa (SEQ ID NO: 24)

5'-uuuagcuucgggucaaugcacacuu (SEQ ID NO: 25)

Pair f

5'-cauugacccgaagcuaaaguggauu (SEQ ID NO: 26)

5'-aauccacuuuagcuucgggucaaug (SEQ ID NO: 27)

Pair g

5'-cgaagcuaaaguggauucaggagua (SEQ ID NO: 28)

5'-uacuccugaauccacuuuagcuucg (SEQ ID NO: 29)

Pair h

5'-ucaggaguaccuggagaaagcuuua (SEQ ID NO: 30)

5'-uaaagcuuucuccagguacuccuga (SEQ ID NO: 31)

Pair i

5'-caggaguaccuggagaaagcuuuaa (SEQ ID NO: 32)

5'-uuaaagcuuucuccagguacuccug (SEQ ID NO: 33)

Pair j

5'-aggaguaccuggagaaagcuuuaaa (SEQ ID NO: 34)

5'-uuuaaagcuuucuccagguacuccu (SEQ ID NO: 35)

These oligonucleotide pairs are incubated with the CXCR4-containing ARPE4-19 cells are transfected with oligonucleotides of each pair listed above, as described above. siRNA inhibition of CXCR4 expression in ARPE-19 cells inhibits the cell death induced by oxidative stress (exposure to 300 uM t-BH) in a dose-dependent fashion. A WST cell viability assay is performed using naive cells or cells exposed to t-BH for 6 hours and transfected either with control oligonucleotides or with siRNA oligonucleotides at 10 nM or 25 nM. Additionally, the siRNA pairs tended to lessen or substantially inhibit CXCR4 expression in treated cells as opposed to control cells not given the siRNA oligonucleotides. This suggests that the anti-CXCR4 siRNA oligonucleotides will be a useful agent in preventing RPE and retinal neurodegeneration.

Example 5

Human breast cancer cell line MDA-MB-435s (which expresses SDF-1) is cultured in microtiter dishes and aliquots transfected with one of the following anti SDF-1 siRNA oligonucleotide pairs.

Pair a

5'-ccagagccaacgucaagcaucucaa (SEQ ID NO: 16)

5'-uugagaugcuugacguuggcucugg (SEQ ID NO: 17)

Pair b

5'-cagagccaacgucaagcaucucaaa (SEQ ID NO: 18)

5'-uuugagaugcuugacguuggcucug (SEQ ID NO: 19)

Following transfection, the cells are prepared for analysis of total SDF-1 mRNA by DNA array. The results show that SDF-1 specific mRNA is substantially reduced in anti-SDF-1 siRNA transfectants.

Example 6

A patient suffering from exudative age related macular degeneration in the right eye is given a subretinal injection of a biodegradable implant containing 1 μg total of equimolar amounts of oligonucleotide pair 4 (SEQ ID NO: 36 and SEQ ID NO: 37) in a volume of 100 μl. The eye is monitored weekly for 16 weeks. By week 3, the patient displays a two line improvement in visual acuity; this increase is maintained throughout the testing period. At the end of the 16 week period no increase in the extent of macular degeneration is observed.

Example 7

Figure 4:
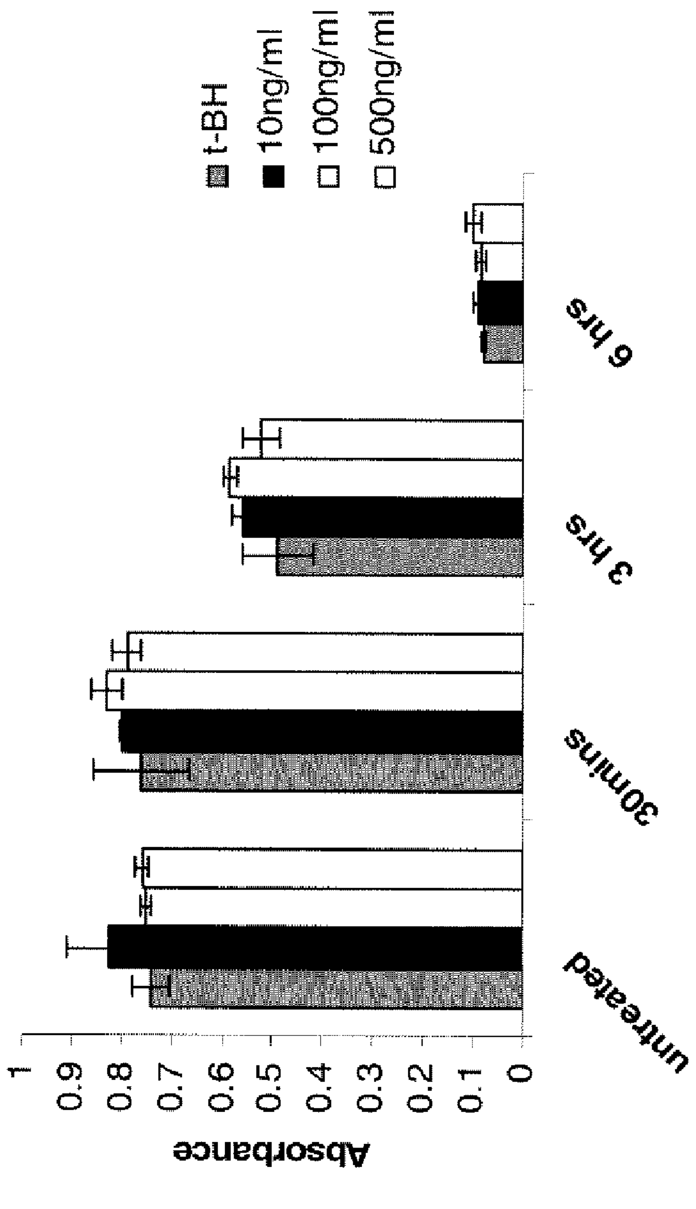
FIG. 4 shows that the addition of recombinant human SDF-1.alpha has no effect on the t-BH-stimulated decrease in ARPE-19 cell viability.

ARPE-19 cells were cultured as described in Example 1 above. The cells were exposed to recombinant human SDF-1α at 10, 100, and 500 ng/ml for 1 hour before addition of the stressor. t-BH was then added, for 0, 30 minutes, 3 hours and 6 hours. The media was the changed and the cells incubated further for a total of 24 hrs from the initiation of t-BH treatment following which a WST cell viability assay was conducted. As shown in FIG. 4, the addition of recombinant human SDF-1α had no effect on the t-BH-stimulated decrease in ARPE-19 cell viability.

Example 8

A 72 year old male patient is diagnosed with exudative age-related macular degeneration. With monitoring visits spaced three months apart, the progression of the disease increases, with the left eye showing a statistically significant loss in visual acuity between visits, and the right eye showing no change.

The patient is given an subconjunctival injection of a solution containing 10 mg of 1,1'-[1,4,phenylene-bis(methylene)]-bis-1,4,8,11-tetraazacyclotetradecane (AMD3100), see Bridger et al., US2004/0209921, incorporated by reference herein) in each eye once every two weeks for 6 months. The patient is monitored bimonthly and visual acuity tested.

At the end of the six-month treatment period, the patient is tested, and displays an increase in visual acuity of two lines in the right eye and one line in the left eye. Fluorescein angiography reveals no detectable leakage of blood into retinal tissues from surrounding blood vessels, and there is no increase in the visibly apparent extent of retinal degeneration from the beginning of the study.

Example 9

A 69 year old female complains of vision loss in the left eye. The patient reports an onset of Type II diabetes at age 40, and has been under treatment with metformin hydrochloride for 10 years. Retinal examination of the left eye under dilation reveals exudative neovascularization and apparent macular edema consistent with a diagnosis of proliferative diabetic retinopathy. Examination of the right eye shows small hemorrhages and microaneurisms in the retinal blood vessels, consistent with a diagnosis of non-proliferative diabetic retinopathy.

The patient is given an intravitreal injection comprising 150 μl of a solution of hyaluronic acid in which biodegradable PLGA microspheres (mean particle diameter of about 40 μm; lactide to glycolide ratio 75:25) are suspended. See U.S. patent application Ser. No. 11/368,845, filed Mar. 6, 2006, incorporated by reference herein in its entirety. Approximate weight of microspheres per dose was 20 mg. In addition to the PLGA polymer, the microspheres comprise approximately 5% by weight of an SDF-1α derivative that comprises a disulfide-linked dimer comprising two identical peptides, with each peptide comprising amino acids 1-9 of SDF-1 (these positions correspond to amino acids 22-47 of SEQ ID NO: 4, 5, and 6) with glycine substituted for proline in each position 2 (corresponding to position 23 of SEQ ID NO: 4, 5, and 6).

This dimer is designated SDF-1 (1-9[P2G]$_2$ (see e.g., Clark-Lewis U.S. Patent Publication No. US 2005/0164935), which is incorporated by reference herein. The substitution of proline for glycine in SDF-1α or β appears sufficient to convert an CXCR4 agonist into a CXCR4 antagonist.

The microparticles are formulated to release up to about 40% of SDF-1 (1-9[P2G]$_2$ in the first few days, with a subsequent release of from about 1% to about 2% over the remaining life of the microspheres.

The patient's visual acuity (and retinal condition under dilation) are monitored every two weeks for 8 weeks. At the end of this period of time, the patient's macular edema is seen to have largely subsided, while no new neovascularization is observed in the left eye. Fluorescein angiography reveals that hemorrhaging has been halted, and visual acuity has increased by three lines in the left eye and 1 line in the right eye.

Example 10

The patient of Example 9 is treated by subconjunctival injection in each eye (100 μl volume in hyaluronic acid solution) of a single fibrous monolithic PLGA intraocular implant (approximately 120 μg; diameter approximately 3 mm) comprising 50% by weight of a CXCR4-inhibitory compound: N-[(S)-1-(1-naphthyl)ethyl]-5-(2-methylbenzyl)amino-2-(S)-[4-[N-(imidazole-2-ylmethyl)aminomethyl]benzoyl] aminopentanoylamide (see Yamzaki et al., U.S. Publication No. 2004/0254221.

After 6 weeks the patient is monitored, and the macular edema is barely observable. Fluorescein angiography does not reveal any leakage of blood into the retina. After 8 weeks visual acuity is tested, and has improved by 2 lines in each eye.

Example 11

The patient of Example 9 is administered an intravitreal injection in each eye comprising 150 μl of a solution of hyaluronic acid in which biodegradable PLGA microspheres (mean particle diameter of about 40 μm; lactide to glycolide ratio 75:25) are suspended. Approximate weight of microspheres per dose was 20 mg. In addition to the PLGA polymer, the microspheres comprise approximately 5% by weight of a CXCR4 inhibitory monoclonal antibody (termed 12G5; see Hoxie, U.S. Pat. No. 5,994,515, incorporated by reference herein.) Approximately 40% of this antibody is released in the first 3 days after injection, and about 1% per day thereafter.

After 6 weeks the treatment is repeated. At the end of 18 weeks the patient is tested. Fluorescein angiography shows no leakage of blood into the retina, and the extent of neovascularization has decreased. Visual acuity has increased 3 lines in the left eye and 2 lines in the right eye.

It will be understood that a variety of modifications or derivatives may be made to the oligonucleotides disclosed herein, such as stabilization against nuclease activity using, for example, phosphorothioate, methylphosphonate, 2'O-methyl sugar modifications, peptide nucleic acids and the like. All such variations fall within the scope of the present invention.

Similarly, as mentioned above, peptide and polypeptide agents may comprise naturally occurring amino acids, optical isomers thereof, or non-naturally occurring or rare amino acids or peptidomemetics.

The foregoing examples serve solely to augment the disclosure of other parts of the specification, including the claims. As such these examples illustrate certain embodiments of the invention, but do not limit it.

All publications, patents and patent applications mentioned in this specification are indicative of the level of skill of those skilled in the art to which this invention pertains. All publications, patents and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications will be immediately apparent to, and may be practiced by, the person of ordinary skill in the art within the scope of the claims following this disclosure.

It will be understood that a variety of modifications or derivatives may be made to the oligonucleotides disclosed herein, such as stabilization against nuclease activity using, for example, phosphorothioate, methylphosphonate, 2'O-methyl sugar modifications, and the like. All such variations fall within the scope of the present invention.

The foregoing examples serve only to illustrate certain embodiments of the invention, which is not limited thereby, but is defined solely by the claims that conclude this specification.

What is claimed is:

1. A method of reducing the rate of progression of a retinal disorder in a mammal, comprising: administering to the retinal tissue of a mammal in need of such reducing a composition comprising a CXCR4 inhibitor, wherein the inhibitor is an antibody or fragment thereof that will selectively bind to CXCR4, and wherein the binding of said antibody inhibits the cellular activity of CXCR4.

2. The method of claim 1 wherein said inhibitor comprises a humanized synthetic antibody fragment.

3. The method of claim 1, wherein the retinal disorder is non-exudative age related macular degeneration.

4. The method of claim 1, wherein the retinal disorder is exudative age related macular degeneration.

5. The method of claim 1, wherein the retinal disorder is macular edema.

6. The method of claim 1, wherein the retinal disorder is diabetic retinopathy.

7. The method of claim 1 wherein said inhibitor comprises an CXCR4 antagonist comprising a binding region of a natural or synthetic polyclonal or monoclonal antibody.

8. The method of claim 7 wherein said inhibitor comprises an antibody fragment selected from the group consisting of an anti CXCR4 Fab fragment, an anti CXCR4 Fab' fragment and recombinant derivatives of one of these.

9. The method of claim 7 wherein said CXCR4 antagonist comprises an anti-CXCR4 antibody variable region.

10. The method of claim 7, wherein the retinal disorder is non-exudative age related macular degeneration.

11. The method of claim 7, wherein the retinal disorder is exudative age related macular degeneration.

12. The method of claim 7, wherein the retinal disorder is macular edema.

13. The method of claim 7, wherein the retinal disorder is diabetic retinopathy.

* * * * *

UNITED STATES PATENT AND TRADEMARK OFFICE

CERTIFICATE OF CORRECTION

PATENT NO. : 7,964,191 B2
APPLICATION NO. : 11/670883
DATED : June 21, 2011
INVENTOR(S) : Gerard A. Rodrigues et al.

It is certified that error appears in the above-identified patent and that said Letters Patent is hereby corrected as shown below:

On Sheet 2 of 4, in Figure 2, on X-axis, line 1, delete "SiRNA" and insert -- siRNA --, therefor.

In column 1, line 56, delete "exudive" and insert -- exudative --, therefor.

In column 1, line 56, delete "diciform" and insert -- disciform --, therefor.

In column 1, line 66, delete "chronicchromic" and insert -- chronic --, therefor.

In column 7, line 18, delete "CXCR4:" and insert -- CXCR4. --, therefor.

In column 7, line 44, delete "Publicaiton" and insert -- Publication --, therefor.

In column 13, line 41, delete "Wherein" and insert -- wherein --, therefor.

In column 15, line 57, delete "isonicotiniamide," and insert -- isonicotinamide, --, therefor.

In column 17, line 55, delete "opthalmia;" and insert -- ophthalmia; --, therefor.

In column 25, line 9-23, after "(SDF-1ß)" delete "SEQ ID NO: 1 megisiytsd nyteemgsgd ydsmkepcfr eenanfnkif lptiysiifl tgivgnglvi lvmgyqkklr smtdkyrlhl svadllfvit lpfwavdava nwyfgnflck avhviytvnl yssvlilafi sldrylaivh atnsqrprkl laekvvyvgv wipallltip dfifanvsea ddryicdrfy pndlwvvvfq fqhimvglil pgivilscyc iiisklshsk ghqkrkalkt tvililaffa cwlpyyigis idsfilleii kqgcefentv hkwisiteal affhcclnpi lyaflgakfk tsaqhaltsv srgsslkils kgkrgghssv stesesssfh ss".

In column 29, line 36, delete "□Minneapolis," and insert -- Minneapolis, --, therefor.

In column 29, line 62, delete "Al.," and insert -- al., --, therefor.

In column 30, line 21, delete "UTR" and insert -- UTR. --, therefor.

Signed and Sealed this
Thirteenth Day of September, 2011

David J. Kappos
*Director of the United States Patent and Trademark Office*

In column 32, line 14, delete “Serpignous” and insert -- Serpiginous --, therefor.

In column 32, line 61, delete “cilary” and insert -- ciliary --, therefor.

In column 34, line 41, delete “biguanidebigunanide” and insert -- biguanidebiguanide --, therefor.

In column 34, line 42, delete “biguanidebiguandide” and insert -- biguanidebiguanide --, therefor.

In column 35, line 6, delete “scleraschlera” and insert -- schleraschlera --, therefor.

In column 35, line 11, delete “nor” and insert -- not --, therefor.

In column 35, line 39, delete “lyophylization” and insert -- lyophilization --, therefor.

In column 36, line 37, delete “glycolproteins,” and insert -- glycoproteins, --, therefor.

In column 42, line 67, delete “uveitus.” and insert -- uveitis. --, therefor.

In column 43, line 13, delete “Delbecco’s” and insert -- Dulbecco’s --, therefor.

In column 44, line 50, delete “Technnologies,” and insert -- Technologies, --, therefor.

In column 44, line 66, delete “pyrrophosphatase,” and insert -- pyrophosphatase, --, therefor.

In column 47, line 25-66, and in column 48, line 1-6, below “Pair 13

5'-aaagcgagguggacauucaucuguu (SEQ ID NO: 54)
5'-aacagaugaauguccaccucgcuuu (SEQ ID NO: 55)”

delete “Pair c

5'-acacuccaaacugugcccuucagau (SEQ ID NO: 20)
5'-aucugaagggcacaguuuggagugu (SEQ ID NO: 21)

Pair d

5'-caagugugcauugacccgaagcuaa (SEQ ID NO: 22)
5'-uuagcuucgggucaaugcacacuug (SEQ ID NO: 23)

Pair e

5'-aagugugcauugacccgaagcuaaa (SEQ ID NO: 24)
5'-uuuagcuucgggucaaugcacacuu (SEQ ID NO: 25)

Pair f

5'-cauugacccgaagcuaaaguggauu (SEQ ID NO: 26)
5'-aauccacuuuagcuucgggucaaug (SEQ ID NO: 27)

Pair g

5'-cgaagcuaaaguggauucaggagua (SEQ ID NO: 28)
5'-uacuccugaauccacuuuagcuucg (SEQ ID NO: 29)

Pair h

5'-ucaggaguaccuggagaaagcuuua (SEQ ID NO: 30)
5'-uaaagcuuucuccagguacuccuga (SEQ ID NO: 31)

Pair i

5'-caggaguaccuggagaaagcuuuaa (SEQ ID NO: 32)
5'-uuaaagcuuucuccagguacuccug (SEQ ID NO: 33)

Pair j

5'-aggaguaccuggagaaagcuuuaaa (SEQ ID NO: 34)
5'-uuuaaagcuuucuccagguacuccu (SEQ ID NO: 35)”.

In column 48, line 34-39, below “Pair b

5'-cagagccaacgucaagcaucucaaa (SEQ ID NO: 18)
5'-uuugagaugcuugacguuggcucug (SEQ ID NO: 19)”

insert -- Pair c

5'-acacuccaaacugugcccuucagau (SEQ ID NO: 20)
5'-aucugaagggcacaguuuggagugu (SEQ ID NO: 21)

Pair d

5'-caagugugcauugacccgaagcuaa (SEQ ID NO: 22)
5'-uuagcuucgggucaaugcacacuug (SEQ ID NO: 23)

Pair e

5'-aagugugcauugacccgaagcuaaa (SEQ ID NO: 24)
5'-uuuagcuucgggucaaugcacacuu (SEQ ID NO: 25)

Pair f

5'-cauugacccgaagcuaaaguggauu (SEQ ID NO: 26)
5'-aauccacuuuagcuucgggucaaug (SEQ ID NO: 27)

Pair g

5'-cgaagcuaaaguggauucaggagua (SEQ ID NO: 28)
5'-uacuccugaauccacuuuagcuucg (SEQ ID NO: 29)

Pair h

5'-ucaggaguaccuggagaaagcuuua (SEQ ID NO: 30)
5'-uaaagcuuucuccagguacuccuga (SEQ ID NO: 31)

Pair i

5'-caggaguaccuggagaaagcuuuaa (SEQ ID NO: 32)
5'-uuaaagcuuucuccagguacuccug (SEQ ID NO: 33)

Pair j

5'-aggaguaccuggagaaagcuuuaaa (SEQ ID NO: 34)
5'-uuuaaagcuuucuccagguacuccu (SEQ ID NO: 35) --.

In column 49, line 36, delete “microaneurisms” and insert -- microaneurysms --, therefor.

In column 49, line 51, delete “6)” and insert -- 6), --, therefor.

In column 50, line 49, delete “peptidomemetics.” and insert -- peptidomimetics. --, therefor.